US011889994B2

(12) United States Patent
Lafon et al.

(10) Patent No.: US 11,889,994 B2
(45) Date of Patent: *Feb. 6, 2024

(54) MENSTRUAL CYCLE TRACKING

(71) Applicant: Fitbit, Inc., San Francisco, CA (US)

(72) Inventors: Belen Lafon, San Francisco, CA (US); Chris Hanrahan Sarantos, San Francisco, CA (US); Conor Joseph Heneghan, Campbell, CA (US); Logan Niehaus, Alameda, CA (US); Jaclyn Leverett Wasson, Alameda, CA (US); Peter Colin Dess, San Francisco, CA (US); Amir Bahador Farjadian, Boston, MA (US); Zachary Todd Beattie, Pleasant Hill, CA (US); Atiyeh Ghoreyshi, San Francisco, CA (US); Allison Shih Wu, San Francisco, CA (US)

(73) Assignee: FITBIT, INC., San Francisco, CA (US)

( * ) Notice: Subject to any disclaimer, the term of this patent is extended or adjusted under 35 U.S.C. 154(b) by 274 days.

This patent is subject to a terminal disclaimer.

(21) Appl. No.: 17/013,337

(22) Filed: Sep. 4, 2020

(65) Prior Publication Data
US 2021/0145415 A1 May 20, 2021

Related U.S. Application Data

(63) Continuation of application No. 16/441,536, filed on Jun. 14, 2019, now Pat. No. 10,765,409.
(Continued)

(51) Int. Cl.
A61B 5/01 (2006.01)
A61B 10/00 (2006.01)
(Continued)

(52) U.S. Cl.
CPC ............ A61B 10/0012 (2013.01); A61B 5/01 (2013.01); A61B 5/02055 (2013.01);
(Continued)

(58) Field of Classification Search
CPC ..... A61B 5/01; A61B 5/1118; A61B 5/14546; A61B 5/14551
See application file for complete search history.

(56) References Cited

U.S. PATENT DOCUMENTS

2016/0058428 A1 3/2016 Shinar et al.
2016/0066894 A1 3/2016 Barton-Sweeney
(Continued)

OTHER PUBLICATIONS

Moran et al., "Cardiovascular Functioning During the Menstrual Cycle", Department of Nursing Studies, St. Martin's College, Lancaster LA1 3JD, UK and Unilever Research Colworth, Colworth House, Shambrook, Bedford, MK44 1LQ, UK; Clinical Physiology 20, vol. 6, pp. 496-504, Blackwell Science Ltd., 2000.
(Continued)

Primary Examiner — Marjan Fardanesh
(74) Attorney, Agent, or Firm — Dority & Manning, P.A.

(57) ABSTRACT

Health information for a woman can be used to predict timing of events related to the woman's menstrual cycle. If available, historical cycle information for a woman can be used to predict upcoming cycle events, such as the start and stop of menstruation. To improve the accuracy of those predictions, one or more health metrics are monitored for the woman that can be correlated with the menstrual cycle. These can include, for example, the resting heart rate (RHR), blood oxygen concentration (SpO$_2$) level, and hemoglobin concentration, among other such options. The metrics are monitored over time to determine patterns that can be correlated with menstrual cycle. This information can then be used to update the predictive model, as well as to update
(Continued)

individual event predictions. Information about the predictions, and updates to the predictions, can be surfaced accordingly.

20 Claims, 8 Drawing Sheets

Related U.S. Application Data

(60) Provisional application No. 62/691,355, filed on Jun. 28, 2018.

(51) Int. Cl.
    *A61B 5/0205* (2006.01)
    *A61B 5/11* (2006.01)
    *A61B 5/145* (2006.01)
    *A61B 5/1455* (2006.01)
    *A61B 5/00* (2006.01)
    *A61B 5/024* (2006.01)

(52) U.S. Cl.
    CPC ........ *A61B 5/1118* (2013.01); *A61B 5/14546* (2013.01); *A61B 5/14551* (2013.01); *A61B 5/4815* (2013.01); *A61B 5/681* (2013.01); *A61B 5/742* (2013.01); *A61B 5/02405* (2013.01); *A61B 5/02433* (2013.01); *A61B 2010/0019* (2013.01)

(56) References Cited

U.S. PATENT DOCUMENTS

2016/0113503 A1    4/2016   Benaron
2018/0035982 A1    2/2018   Tholen et al.

OTHER PUBLICATIONS

Seebauer et al., "Changes of Respiratory Sinus Arrhythmia During the Menstrual Cycle Depend on Average Heart Rate", European Journal of Applied Physiology, vol. 87, 2002, pp. 309-314, Springer-Verlag, DOI 10.1007/s00421-002-0634-0.

Shilaih et al., "Pulse Rate Measurement During Sleep Using Wearable Sensors, and its Correlation with the Menstrual Cycle Phases, a Prospective Observational Study", Scientific Reports 7: 1294, DOI:10.1038/s41598-017-01433-9 www.nature.com/scientificreports, pp. 1-7, 2017.

Goodale et al., "Wearable Sensors Reveal Menses-Driven Changes in Physiology and Enable Prediction of the Fertile Window: Observational Study", Journal of Medical Internet Research, vol. 21, No. 4, 2019, pp. 1-15.

International Search Report and Written Opinion issued in related International Application No. PCT/US2019/039230 dated Sep. 18, 2019.

Shah et al., "Noninvasive Functional Optical Spectroscopy of Human Breast Tissue", National Academy of Sciences (PNAS), vol. 98, No. 8, pp. 4420-4425, Apr. 10, 2001.

Pogue et al., "Characterization of Hemoglobin, Water, and NIR Scattering in Breast Tissue: Analysis of Intersubject Variability and Menstrual Cycle Changes", Journal of Biomedical Optics, vol. 9, No. 3, pp. 541-552, Jan. 1, 2004.

Requirement for Restriction issued in U.S. Appl. No. 16/441,536 dated Jul. 18, 2019.

Non-Final Office Action issued in U.S. Appl. No. 16/441,536 dated Oct. 24, 2019.

Notice of Allowance issued in U.S. Appl. No. 16/441,536 dated Aug. 10, 2020.

MENSTRUAL CYCLE TRACKING

CROSS-REFERENCE TO RELATED APPLICATIONS

This Non-Provisional Patent Application is a continuation of U.S. Non-Provisional application Ser. No. 16/441,536, filed Jun. 14, 2019, which claims priority to, and the benefit of, allowed U.S. Provisional Patent Application No. 62/691,355 filed Jun. 28, 2018, which is hereby incorporated by reference herein in its entirety.

BACKGROUND

Recent advances in technology, including those available through consumer devices, have provided for corresponding advances in health detection and monitoring. For example, devices such as fitness bands and smart watches are able to determine information relating to the pulse or motion of a person wearing the device. Due to capabilities of conventional devices, however, the amount and types of health information able to be determined using such devices has been limited. Accordingly, much tracking or health monitoring done using these devices relies primarily upon user input.

BRIEF DESCRIPTION OF THE DRAWINGS

Various embodiments in accordance with the present disclosure will be described with reference to the drawings, in which.

DETAILED DESCRIPTION

Figure 1A:
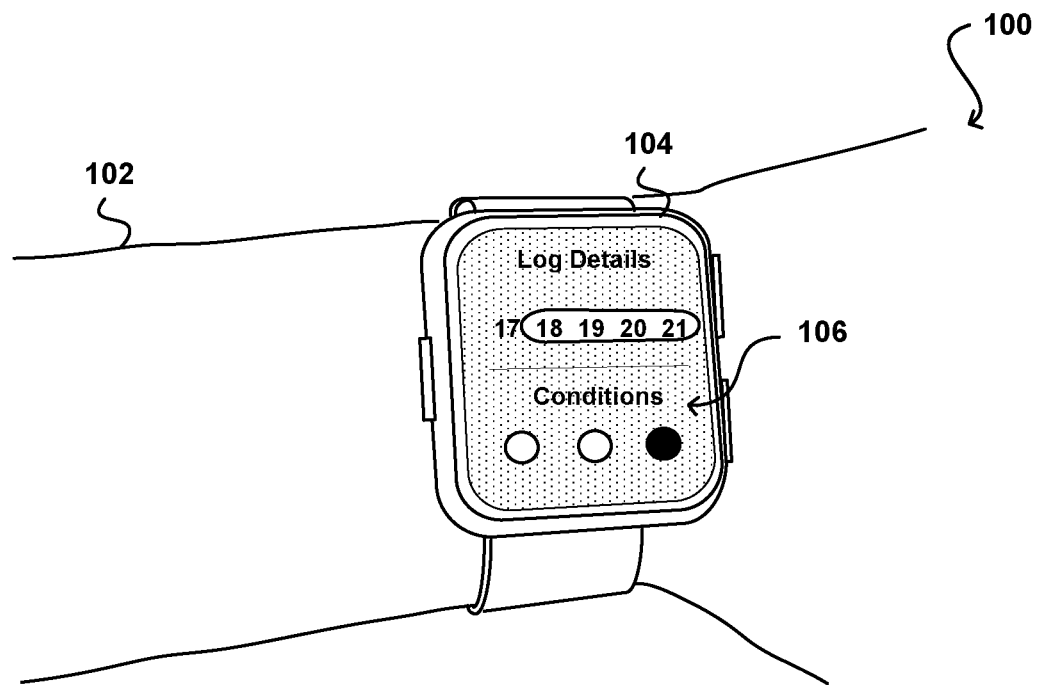
FIGS. 1A and 1B illustrate an example device that can be used to obtain and analyze user health information in accordance with various embodiments.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Approaches in accordance with various embodiments provide for automated health monitoring, and in particular relate to the automated tracking of menstrual cycles and related health information. In some embodiments, historical cycle information can be obtained for a user that can contain information such as the start and stop dates for menstruation over a number of past cycles. This information can be used to predict/detect upcoming/previous menstrual cycle events, such as the start and/or stop of ovulation or menstruation. In order to improve the accuracy of those predictions, one or more health metrics can be monitored for the user that can be correlated with the menstrual cycle. These can include, for example, the resting heart rate (RHR) and/or other heart rate-derived data, blood oxygen concentration ($SpO_2$) level, heart rate variability metrics (HRV), sleep duration and quality, exercise levels, weight, hemoglobin and water concentration, as well as concentration of oils/lipids/collagen in and on the skin, among other such options. One or more of these health metrics can be monitored over time to determine patterns or cycles of variation in the metrics, which can be correlated with a woman's menstrual cycle. This information can then be used to update the predictive model, as well as to update individual event predictions based at least in part upon the current values of those metrics for the woman. Information about the predictions, and updates to the predictions, can be surfaced to the user, which can help with planning around events such as menstruation and ovulation, which can be important for woman trying to conceive or trying to avoid conception, among other such reasons. Such information can also be used to provide "insights" to a user. For example, sleep data can be analyzed and a determination can be made that the user is sleeping poorly during one portion of her menstrual cycle. The user can then be provided with information about this determination, as well as various suggestions as to potential remedial actions. Another example insight relates to weight monitoring. For example, the system can analyze weight gain and loss during the menstrual cycle and inform a user about expected weight fluctuations during the user's menstrual cycle. Data can also be analyzed to provide other insights as to various symptoms or states when correlations are identified, such as to convey to a user that when she exercises she will suffer less pain from cramping. This data can be useful for performance training whereby an athlete can modify her training regimen based on menstrual cycle information. For example, she may plan intense workouts on certain days and less-intense workouts on other days.

Various other functions can be implemented within the various embodiments as well as discussed and suggested elsewhere herein.

For various reasons, it can be desirable to track the temporal pattern of menstrual cycles in women in an automated and non-invasive fashion. It can also be desirable that such tracking can be performed with minimal intervention required by the user (or patient, etc.). Conventional approaches to tracking menstrual cycle rely on manual entry or annotation by an individual who will typically rely on direct visual evidence of bleeding. Other factors can be used to make such a determination as well, such as the use of body temperature readings as a guide to a woman's fertility window and ovulation. An advantage of developing an automated system lies in the fact that the tracking of menstrual cycles is recommended by doctors as a general health indicator for women, as significant deviations may be indicative of underlying health issues. Performing the measurements automatically can remove opportunity for user error, which may result from inputting incorrect information or inputting information inconsistently. Such a system may also provide useful guidance to women in terms of predicting when significant events such as menstruation or ovulation will occur, so they can plan around such events.

In various embodiments discussed herein, a woman can wear or utilize a device that is able to automatically measure or determine aspects of the health or wellbeing of the woman. An example of such a device is a smart watch 104 illustrated in FIG. 1A, although other devices such as smart or connected fitness bands, watches, rings, earbuds, phones, clothing, and the like can be utilized as well within the scope of the various embodiments. In this example, the woman can wear the smart watch 104 on her arm, and can view health information 106 on a display screen of the watch. In many embodiments the display will be a touch sensitive display that will also allow the woman to input or annotate information about her cycle as discussed elsewhere herein.

Figure 1B:
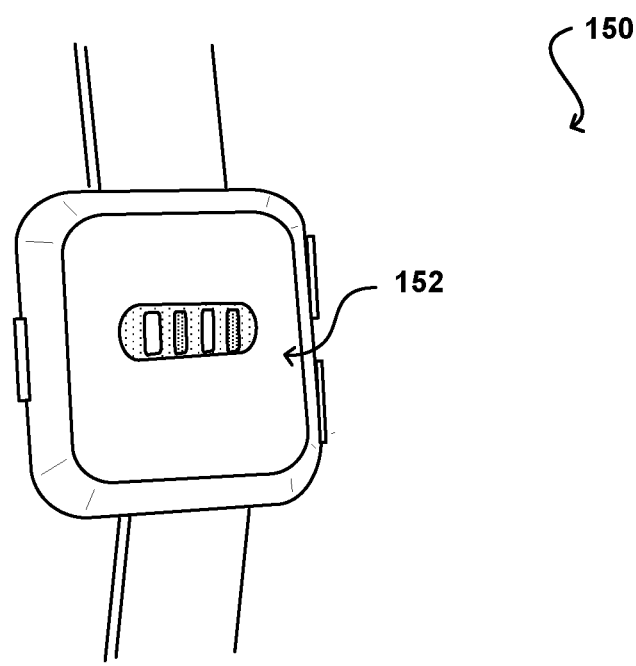

The watch may include various sensors, such as motion and temperature sensors, which can be used to measure or detect information about the user. The watch can also include an optical measurement sub-system 152, such as is illustrated in the example back view of the smart watch 150 illustrated in FIG. 1B. In this example, the optical measurement sub-system includes at least one optical emitter and at least one optical receiver. The emitter can emit light of one or more wavelengths that can be reflected from the surface of the user's skin, or diffusely reflected after traveling, under the surface, and detected by at least one of the emitters. Such an optical assembly can enable the smart watch to measure various types of information during times in which the woman is wearing the smart watch.

In one embodiment, a woman can wear a smart watch that contains an optical photoplethsymogram (PPG) and an accelerometer. The PPG can obtain volumetric measurements by illuminating the skin, such as by using an emitter on a side of the watch proximate the woman's wrist, and measuring a change in absorption of the light over time. The frequency of these changes can be representative of the heart rate or pulse of the user. Because these measurements can be susceptible to motion effects, it may be preferable in at least some embodiments to attempt to determine the resting heart rate (RHR) of the woman. This may be accomplished at night while the woman is sleeping, for example, although other periods of low activity (or even periods that are activity independent) can be used as well within the scope of the various embodiments. The device can determine the heart rate by detecting peaks in the optical signal. The device can apply a low-pass filter to remove noise in the optical signal. In some cases, there may be no clear peaks such that a heart rate cannot be reliably detected, as may be due to excessive motion. For devices that include an accelerometer, inertial sensor, or other such sensor or component, periods of excessive movement can be determined and then excluded from analysis. In other embodiments the data for these periods may still be utilized, but with the motion effects accounted for in the analysis. A sensor such as an accelerometer can also be used to determine the overall sleeping period (e.g., from 11 pm to 7 am). An estimate of the resting heart rate of the woman can then be calculated. In one embodiment a histogram of heart rate values overnight can be generated. A specified measure, such as the tenth percentile of this histogram, can then be taken as a representative value of the resting heart rate (RHR). RHR values can be determined in other ways as well, such as by only using time segments where the user has been still for at least a minimum period of time, such as at least five minutes, and the optical signal as a sufficiently high signal-to-noise ratio.

The RHR value, once determined, can be used to characterize the overall day for that subject. The history of daily resting heart rates can be collected over time, with a plot 200 of such data being illustrated in FIG. 2A. The illustrated plot shows the RHR for an individual over a one year period. The vertical bars 202 in the plot indicate the times during which menstruation occurred. In typical menstruating women, this resting heart rate follows a cycle lasting between twenty-one and thirty-five days with a median of twenty-nine days. The cycle length is driven by factors such as the underlying hormonal changes. For the example illustrated in FIG. 2A, menses is tied with a decreasing rate of values of the RHR, for this subject.

The device, also referred to herein as the tracker, being worn by the woman can calculate heart rate and movement data, although in some embodiments the tracker can capture that data and transmit the data to a separate computing device for analysis, among other such options. The tracker in some embodiments can send the data to a local computing device, such as by using a Bluetooth signal to send the data to a smart phone that can synchronize the data with a remote database server. In embodiments where the tracker has network connectivity, such as through Wi-Fi or a cellular connection, the tracker might synchronize the data to a database server without an intermediate computing device. The data can then be analyzed at the database server, such as by using a prediction and recording algorithm. The output of the algorithm can be fed back to an application executing on the user's phone or tracker, among other such options. The device can preprocess the data or send raw observations to the database server. In some embodiments the app can present a calendar view that can show historical cycle data, such as may correspond to the dates when menstruation occurred in the past. The view can also indicate predicted times or dates for future menstruation based on the prediction values. Other information can be surfaced or available as well, as may relate to predicted times of ovulation or fertile windows, and in some instances even periods during which menstrual cycle related symptoms such as PMS are likely to be encountered.

In one embodiment a user interface can automatically populate a calendar with the likely start date of the menses, and the most likely date of ovulation as well as the fertile window. The user interface can also provide the capability for the woman to enter the actual events as she experiences them (e.g. start and end of menses, ovulation, etc.). This user feedback can be used to improve the accuracy of any recording or prediction. The system can also incorporate a predictive element, which uses the previous history to predict the likely menstrual cycle in the future. In one embodiment, a system can utilize an autoregressive moving average (ARMA) model of the RHR. The ARMA model can be used to predict the likely dates of menstruation. In an example ARMA model, the RHR is modeled as a combination of sinusoidal frequencies. Given a set of historical data, optimum values for the coefficients $w_0$ can be determined. These coefficients can then be used to predict the future RHR, such as may be based on the historical record of when menstruation occurs relative to peaks and troughs in the RHR pattern.

Alternative prediction algorithms can take as input a set of previous start dates of menstruation (t1,t2, t3, etc.), as well as the resulting calculated menstrual cycle lengths ((t2-t1), (t3-t2), . . . ). A multi-regression equation can then be used which takes as input the previous cycle lengths plus the RHR from a recent section of time, in order to predict the most likely next period duration. The duration in one embodiment can then be given by:

$$P_n = f(P_{n-1}, P_{n-2}, P_{n-3}, RHR)$$

where RHR is a vector of the resting heart rate values from previous days. The RHR vector can be thirty days of data, one year of data, etc. as well as all data available for the user. The system can use heart rate variability (HRV) metrics, and/or PPG-derived metrics in place of, or in addition to, the resting heart rate. Heart rate-derived data can include heart rate (HR), heart rate variability (HRV), resting heart rate (RHR), electrocardiogram (ECG/EKG), atrial fibrillation (AFib), etc. Sensor data can include data for skin/body temperature, impedance cardiography, electrodermal activity (EDA), glucose levels, etc. While $P_n$ is shown above as being dependent on $P_{n-1}$ (e.g., a previous prediction) $P_n$ can be additionally or alternatively dependent on confirmed cycle data.

Other alternative algorithms include a regression algorithm to predict how many days up to the day of next menses. The classification technique can be a non-linear regressor such as, but not limited to, gradient boost regression, random forest regression, logistic regression, and support vector machine regression. The features can include any of the variables mentioned elsewhere herein. A convolutional neural network can be designed to extract HR metrics during sleep that varies in correlation with the menstrual cycle and improves prediction accuracy. The CNN can be trained on data during different sleep stages and the optimal sleep stage can be determined to predict menstrual cycle events such as menses, ovulation, or fertile window. A long short term memory neural network (LSTM), hidden Markov model, or other time series model can be designed to predict events of the next menstrual cycle based on previous menstrual cycle history, this model can also take into account any of the appropriate variables discussed herein. Multiple LSTM models can be trained to predict different parts of the menstrual cycle in various embodiments. Certain techniques can be used to classify days as likely being associated with cycle events. Such classification of past days (e.g., for detection) and future days (e.g., for prediction) can be useful in a variety of circumstances.

Heart rate variability (HRV) can be calculated in some embodiments by first determining the time intervals between successive heartbeats. The detected photoplethsyomogram (PPG) peaks or troughs can be used to form a peak-to-peak (PP) time series. The variability of the PP series can reflect the control of the heart, and to a much smaller extent the influence of the autonomic nervous system on the blood vessel compliance. Main influences on the PP interval can include the parasympathetic nervous system (whose activation tends to slow the heart rate and hence lengthen PPG) and the sympathetic nervous system (whose activation tends to speed up the heart and shorten PP interval). The parasympathetic (PS) and sympathetic systems can operate on slightly different time-scales. Specifically, the PS system can operate on a very short time scale and affect the next beat while the sympathetic system is mediated through acetylcholine and takes multiple beats to take effect. One way to capture this difference is to take the spectral density of the PP series using a technique called Heart Rate Variability (HRV) analysis. The higher-frequency components of the spectrum will reflect the parasympathetic activation since they correspond to short time scales, while lower frequency components reflect both parasympathetic and sympathetic effects. Hormonal changes associated with the menstrual cycle are associated with changes in the autonomic nervous system, and hence can influence heart rate variability. In one embodiment, HRV parameters such as low frequency (LF) and high frequency (HF) power can be calculated.

One convention is to define a HF band between 0.15 Hz and 0.4 Hz, as well as a LF band between 0.05 Hz and 0.15 Hz in the power spectral density estimate. Further discussion of approaches for defining these frequencies can be obtained from co-pending U.S. patent application Ser. No. 15/438,643, filed Feb. 21, 2017, and entitled "Methods and systems for labeling sleep states," which is hereby incorporated herein by reference. Another convention is to ascribe power in the HF band to parasympathetic activation, and power in the LF band to a mixture of sympathetic and parasympathetic activation. Other HRV parameters calculated can include:

ApEn, the approximate entropy of the PP series

SDNN, the standard deviation of NN intervals. Often calculated over a 24-hour period SDANN, the standard deviation of the average NN intervals calculated over short periods, usually 5 minutes. SDANN is therefore a measure of changes in heart rate due to cycles longer than 5 minutes. SDNN reflects all the cyclic components responsible for variability in the period of recording, therefore it represents total variability RMSSD ("root mean square of successive differences"), the square root of the mean of the squares of the successive differences between adjacent NNs SDSD ("standard deviation of successive differences"), the standard deviation of the successive differences between adjacent NNs NN50, the number of pairs of successive NNs that differ by more than 50 ms pNN50, the proportion of NN50 divided by total number of NNs These variables also vary on an approximate number of days similar to the user's menstrual cycle (21-35 days), and the same techniques for fitting a curve to them (e.g., ARMA model) can be used to predict the underlying menstrual cycle length. The independent estimates of cycle length from each of these variables can be combined into a common estimate by a weighting of the variables.

In one embodiment, an overnight heart rate recording for a person can first be divided into various sleep stages, such as may include light sleep, deep sleep, and REM sleep. The HRV parameters and heart rate can then be calculated for a specific stage of sleep only such as the REM stage, rather than for the entire night. A model of the RHR (or a metric derived from HRV) calculated only over the non-REM sections of sleep (e.g., light sleep and deep sleep) can be used to fit the predicted menstrual cycle length.

In another embodiment, a person's breathing rate can be extracted from the PPG signal. The breathing rate would typically be measured to be between twelve and twenty breaths per minute. An average breathing rate can be extracted for each night, or at least a set of nights, and used to fit the underlying menstrual cycle dynamics. Such an approach can also provide the ability for the user to tag events which might be related to the underlying menstrual cycle, including symptoms such as cramps or water retention. The user can also tag lifestyle changes of relevance, such as cutting out certain items from the person's diet, increased amounts of exercise, etc.

Some embodiments can utilize ovulation sticks to provide a gold standard as to when ovulation occurs, and that information can then be entered into the app or otherwise provided.

Similarly, users may use vaginal temperature or body basal temperature as an input for ovulation. A system or service may also incorporate information from a body composition analyzer, or from an electrodermal sensor, to assist in prediction of the menstrual cycle. The user's activity level can also be tracked, which can be used to correct confounders such as heavy exercise, which may affect the resting heart rate and HRV parameters used in the predictor. Other types of activity can also affect a person's cycle. Some embodiments can allow for user input through an app running on a mobile device. For input, the user can select icons (e.g., emojis) which might reflect stress, cramps, degree of bleeding, illness, and mood, among other such options. The output shown to the user may then be a linear/bar graph, or other such indicator. In some embodiments the information can be presented in a circular or calendar format, etc. The information presented can also include predictions as to a start of menstruation, ovulation, duration of menses, fertile window, PMS symptoms, menstrual cycle related symptoms (e.g., cramping, bleeding, etc.), or pregnancy (if there is a change), among other such options. Such a system can also utilize electrodermal measurements as discussed above. Information from other types of devices can be incorporated as well, such as from a chest band or an ECG patch, etc.

Figure 2A:
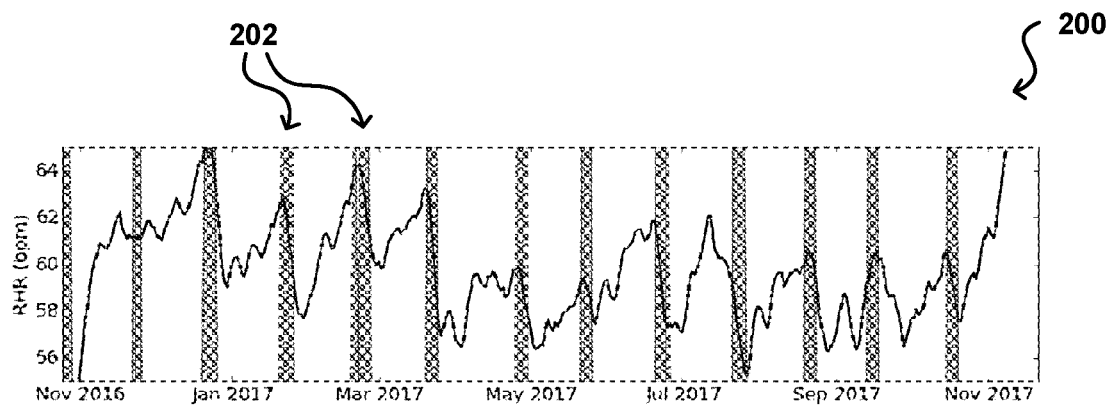
FIGS. 2A and 2B illustrate example plots of heart rate data over time that can be utilized in accordance with various embodiments.
Figure 2B:
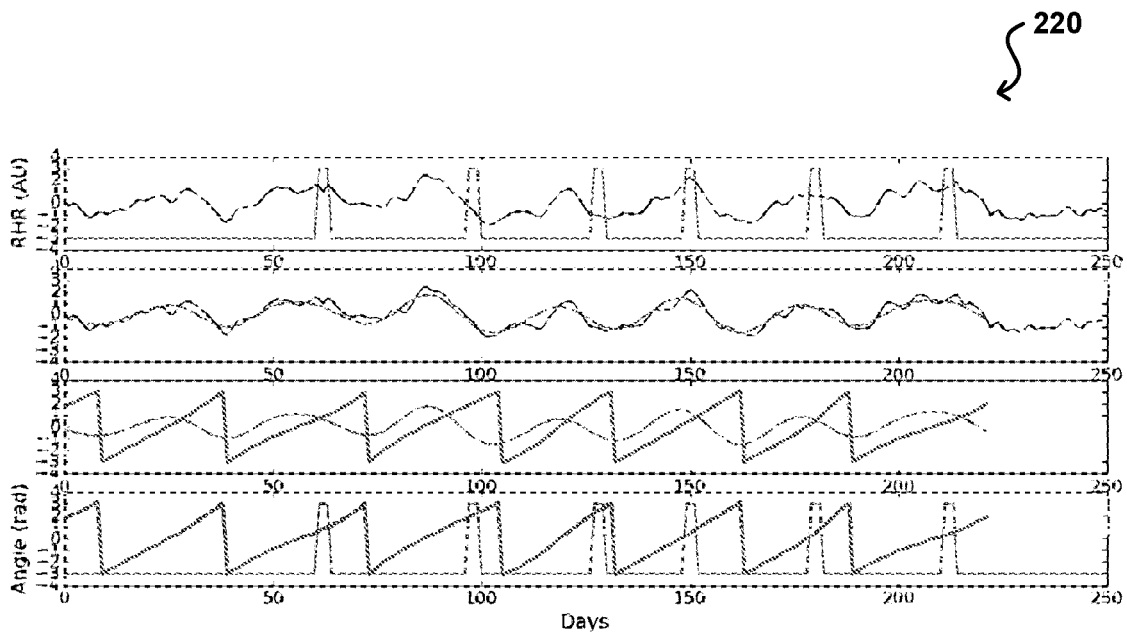

FIG. 2B illustrates a set of plots 220 for determining menstrual cycle time that can be generated in accordance with various embodiments. In this example, the top plot includes the variations in normalized resting heart rate (RHR) over a course of approximately five menstrual cycles. As illustrated, RHR will vary over the course of time but has distinct peaks and valleys that correlate in at least some aspects to the menstrual cycle. The top plot illustrates times of menstruation as peaks in a substantially binary plot, where a set of six peaks is illustrated each having a non-menstruating period between peaks and a peak indicating presence of menstruation over a subset of days for each peak.

In the second plot from the top, a filter (such as a bandpass finite-duration impulse response or "FIR" filter) is applied to the RHR data to produce a smoother RHR curve, which reduces some of the higher frequency noise in the signal. As illustrated, the filtered curve demonstrates clear peaks and valleys correlated to the menstrual cycle. In the third plot from the top, the instantaneous phase of the RHR data is shown. In the bottom blot of FIG. 2B, the phase of RHR can be correlated with the point in the menstrual cycle. With enough data, the RHR phase can be used to improve predictions as to menstrual cycle events, such as the start of menstruation or ovulation, etc.

Figure 3:
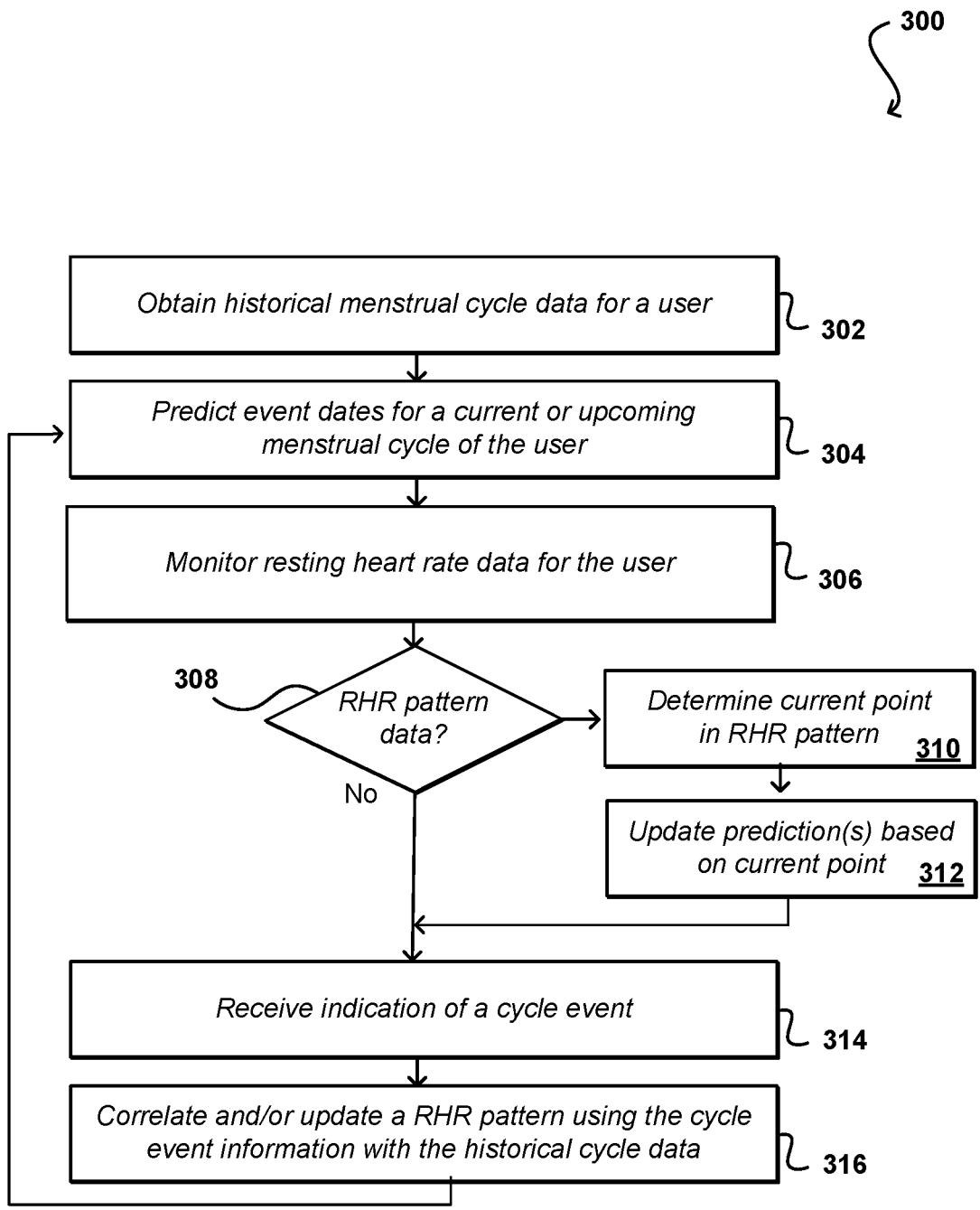
FIG. 3 illustrates an example process for predicting events for a woman's menstrual cycle that can be utilized in accordance with various embodiments.

FIG. 3 illustrates an example process 300 for monitoring health information for a user and using that information to predict timing of events in the user's menstrual cycle that can be utilized in accordance some embodiments. It should be understood for this and other processes discussed herein that there can be additional, alternative, or fewer steps performed in similar or alternative orders, or in parallel, within the scope of the various embodiments unless otherwise stated. In this example, historical menstrual cycle information is obtained 302 for a user. This can include receiving input from the user or obtaining the data from another source, such as from an account or repository associated with a health monitoring device, among other such options. As discussed, this historical information can include date and/or time information for at least the approximate beginning and end times of menstruation, ovulation dates (given by hormonal testing), and other menstrual cycle symptoms over a plurality of past cycles. While in some embodiments a minimum amount of information might be an approximate cycle length, in at least some embodiments a greater amount of information can lead to a more accurate prediction of upcoming cycle dates. In some embodiments an application might provide an electronic diary or journal where a woman can keep track of such dates, and when certain event cycle dates are predicted or detected, a woman might be prompted to confirm the event, etc.

Based at least in part upon the obtained historical data, one or more event dates can be predicted 304 for a current or upcoming menstrual cycle of the identified user. As mentioned, this can be based upon factors such as the average cycle length and the last date of menstruation, among other such factors. Where additional cycle data is available, the predictions may be based upon a pattern of the cycle such that the last date of menstruation may not have significant impact as discussed herein. Other information can be taken into account as well, such as may include age, health, medication, changes in exercise or diet, or other information that may impact the timing of events in the cycle for the user.

Concurrently with the analysis and predictions in at least some embodiments, heart rate information such as the resting heart rate (RHR) can be monitored 306 for the respective user. As mentioned, this may include using the tracking device during a sleep period and after a minimum period of inactivity to obtain RHR date for the user using one or more approaches as discussed and suggested herein. If it is determined 308 that there is no resting heart rate pattern information available, then the process can continue without utilizing such pattern information. In that case, the prediction information for the user may remain unchanged (barring modifications based on other data or input) until such time as indication of a cycle event is received 314. This may include, for example, a user providing input indicating the start of her period or another such occurrence associated with the menstrual cycle. This information can be used to update the historical data and predictions based thereon. Further, the RHR information obtained over the cycle (and any previous cycles) can be analyzed to determine a pattern in variation of RHR for the user, and this pattern can be correlated 316 with the menstrual cycle. As discussed, this can include determining a cyclical pattern of RHR variation, and correlating points in the cyclical pattern that correspond with events in the menstrual cycle, with both cycles typically having a similar duration in time.

Once the correlation is performed, the patterns of RHR variation and menstrual cycle events can be used together to predict 304 (or update predictions for) one or more event dates for a current or upcoming menstrual cycle as discussed herein. The RHR values can continue to be monitored 306 for the user. Since it can be determined 308 that RHR pattern data is available for the user, the current point in the RHR pattern can be determined 310 for various RHR readings, such as may occur once a day based at least in part upon an average or other RHR value generated from that day's HR readings or data. This information can then be used to update 312 the predictions for upcoming cycle events based at least in part upon the point in the RHR cycle. For example, predictions based on cycle dates alone might have an error of plus or minus two days for a certain user. Many users will see an average error of less than two days, but the average errors in some groups may be closer to six days. The RHR data can be used to determine a more accurate time within that window based at least in part upon the correlation of the RHR values with cycle events. In some embodiments, the information will be updated and available to the user. If the likely start of menses or ovulation is changed and is within a specified time window, such as within one or two days of the current time, then a notification might be generated for the user indicating the likely upcoming event. The process can continue with event information being received 314 and the patterns and correlations being updated 316 based at least in part upon the event information. As discussed herein, other factors (e.g., $SpO_2$ level or hemoglobin concentration) can be used instead of RHR in such a process as well within the scope of the various embodiments.

These and other metrics can be used to predict menstrual cycles and related health issues, and in some embodiments combinations of these metrics and approaches can be used to attempt to improve the accuracy of the predictions. In some embodiments, resting heart rate monitoring alone can be used to predict cycle times. This can be done alone, or with input from a user regarding the actual start and stop times for the menstrual cycle. Other information from the user can be input as well, as may relate to symptoms or other health aspects discussed and suggested herein. In some embodiments the user information will be used to make an initial prediction, as discussed above, and the health monitoring information will use this as a starting point to attempt to improve the prediction. In some embodiments the health information will be automatically collected and used to predict menses times, and the user-provided information will provide accuracy information that can be used to refine or retrain the predictive model, such as where machine learning is used to analyze the data and determine the predicted menses times.

While many techniques described herein are discussed as being predictive, for example that a system can be used to predict future menstrual cycle events, such techniques are generally applicable for menstrual cycle event determination. Such menstrual cycle event determination can be associated with events in the past and present (e.g., detection) and/or events in the future (e.g., prediction). Thus, it should be understood that the discussion of techniques used to predict events are equally applicable to detecting past or present events as appropriate. "Determining" can be inclusive of detecting past/present events as well as predicting future events.

In some embodiments, two or more measurements can be combined to attempt to improve the predictions, whether using user input-based predictions as discussed above or based upon measured or detected body and health data alone. For example, in one embodiment a woman's heart rate information and blood or tissue chemistry can be used to predict timing of events related to the woman's menstrual cycle. For example, there may be variations in the concentration or number of red or white blood cells, or the concentration or amount of hemoglobin, ferritin, serum iron, peripheral capillary oxygen saturation ($SpO_2$), water, lipid, collagen, sebum, or other components typically found in a person's blood or skin tissue or the surface of the skin. Variations in body temperature can also be determined using a temperature sensor, as core body and wrist temperature can vary during a woman's cycle as well.

In one embodiment, a tracker in accordance with various embodiments can perform non-invasive real-time measurement of hemoglobin and water content (e.g., a hemoglobin to water ratio, or relative changes in just hemoglobin or water concentration in the blood and tissue) in a woman's body using optical emitters, sensors, and other components such as those discussed and suggested herein. The amount of light absorption in human skin can vary with differences in hemoglobin and water concentration. This can be particularly noticeable for light having wavelengths in the infrared (IR) or near-IR spectrums. As the hemoglobin concentration decreases, the amount of light absorption due to hemoglobin decreases. The amount of light absorption will also change by a different amount based on changes in oxygen saturation, and the absorption differences are more pronounced at different wavelengths. Accordingly, in some embodiments a tracker might include a first emitter at a first wavelength and second emitter at a second wavelength appropriate for detecting variations in hemoglobin and water concentration, while in other embodiments a tracker might include a third emitter at a second wavelength appropriate for detecting variations in $SpO_2$, while some trackers can include both (or an emitter assembly capable of selectively or concurrently emitting light in both target wavelength bands). In one embodiment, a tracker can include two light-emitting diodes (LEDs) with two wavelengths in the range of about 600-1000 nm to detect changes in $SpO_2$ and hemoglobin content, and another LED with a wavelength in the range of 1000-1500 nm for measuring variations in water content, and for measuring hemoglobin to water ratios when combined with one of the first two LEDs.

As with resting heart rate data illustrated in FIG. 2A, values for metrics such as hemoglobin and water concentration and $SpO_2$ can be cyclical, with peaks and valleys that correspond to points in the menstrual cycle. By monitoring how these metrics vary in a woman's body over time and how these variations correspond to the menstrual cycle, measurements of these metrics can be used to predict timing of events for the current menstrual cycle, as well as upcoming menstrual cycles, although variations in a woman's body and surroundings can decrease the accuracy of predictions for cycles further in advance of the current cycle in at least some embodiments. Changes in these parameters also can be indicative or other potential issues in a woman's body, and thus can be used in some embodiments to recommend seeing a doctor or taking another such action.

In some embodiments an application might ask questions of a user in response to detected changes to the user's body. For example, changes in sleep pattern might be due to changes in location or stress that might be independent of the cycle. Other changes, such as new medicines, alcohol consumption, traveling across different time zones, shift change workers, stress, or exercise patterns, might influence at least some of the measurements as well. By obtaining this information, the software can determine whether to exclude certain values or periods of time, whether to weight those values differently, etc. Information available from motion sensors or other activity tracking can also be used to attempt to determine some of these factors as well within the scope of the various embodiments.

Figure 4:
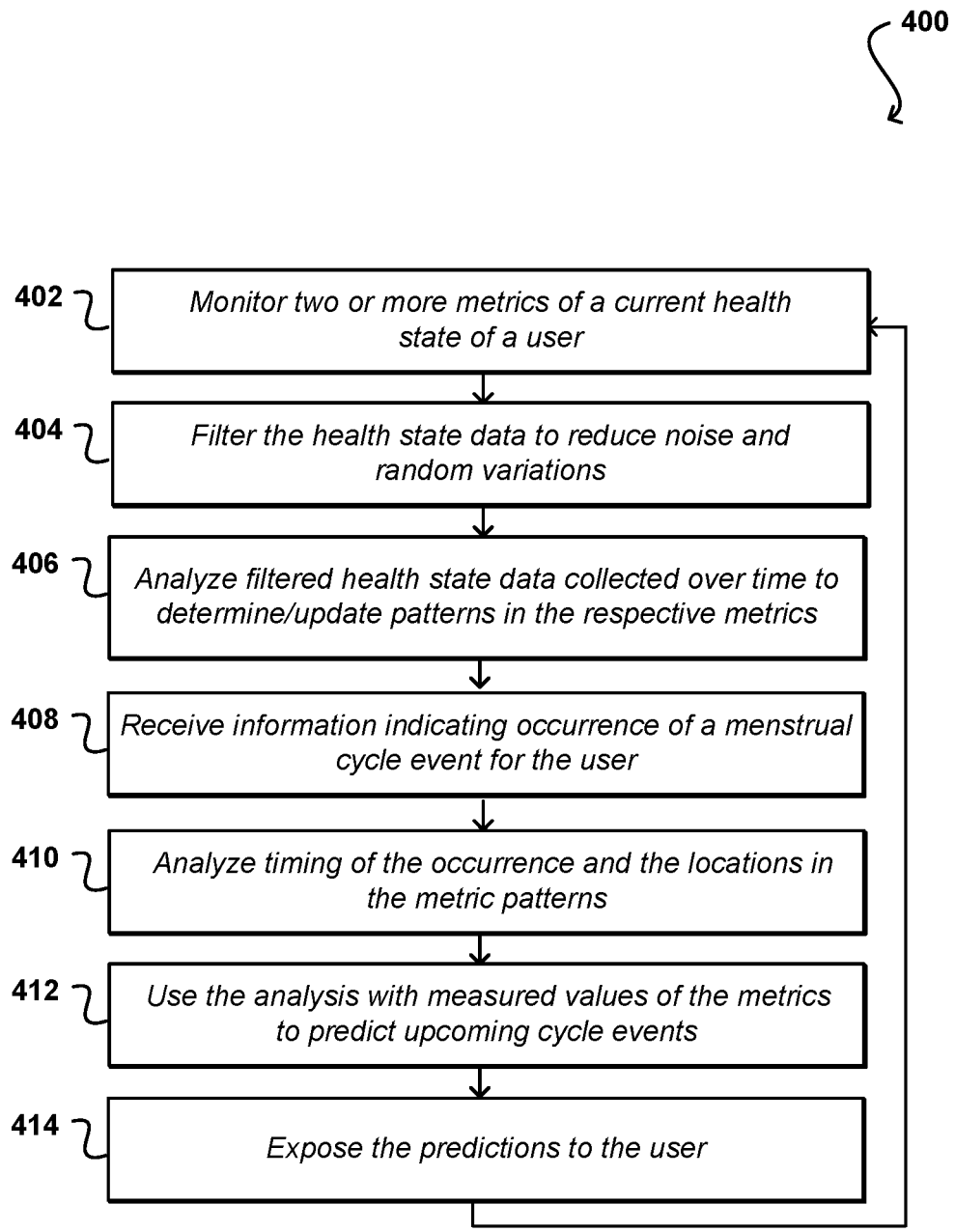
FIG. 4 illustrates another example process for predicting events for a woman's menstrual cycle that can be utilized in accordance with various embodiments.

FIG. 4 illustrates an example process 400 for automatically determining and predicting menstrual cycle information using these and other types of information that can be utilized in accordance with various embodiments. While historical cycle information may be available for use in such a process, the process does not require such information and can make determinations and predictions automatically, without requiring user input, based at least in part upon health information obtained or monitored for the user over time. In this example, two or more metrics for a current health state of a user are monitored 402 over time. As mentioned, these can include metrics that vary with menstrual cycle in at least some embodiments, where those metrics can include metrics discussed or suggested herein including, but not limited to, RHR, $SpO_2$, hemoglobin concentration, water retention, skin sebum or collagen content, lipid content in blood or interstitial tissue, sleep logging, sleep quality, sleep duration, sleep stages architecture (including but not limited to wake after sleep onset, total time in bed, total awake time), HRV metrics during the day and during sleep, HR derived metric, time spent in different HR zones, breathing rate, active minutes, exercise logging, altimeter changes, step count, food logs, water logs, weight measurements, body mass index, body impedance analysis, mood logs, symptom logging (cramps, headache, sick, tender breasts, bloating, and acne), manual exclusion of a cycle log, cervical fluid logging, sexual activity logging, morning-after pill use logging, changes in time zones, location, wrist temperature, body basal temperature, oral temperature, in-ear temperature, hormonal levels as detected by urine or blood test samples, PPG-derived features, and the like. For this example, the process will discuss a combination of RHR and hemoglobin measurements, but it should be understood that this is only one example embodiment and that other combinations or types of information can be used as well within the scope of the various embodiments.

In this example, the data for the RHR and hemoglobin concentrations can be collected using a selection of optical sensors as discussed herein, although other approaches can be used as well. The data can be collected over time and filtered 404 to reduce noise and random variations in the data, which may be due to natural variations as well as outside influences such as changes in exercise, diet, stress, and the like. Other types of processing of the data can be used as well as would be apparent to one of ordinary skill in the art in light of the teachings and suggestions contained herein. The filtered data collected over time can be analyzed 406 to determine or update patterns determined for the respective metrics. This can include updating pattern information based on additional data to obtain more accurate pattern information. In some embodiments, the health state data may be weighted or decayed such that recent health data has more of an impact on pattern determination to account for changes in the health of the user, such as changes in age, hormone levels, etc. While information for a single cycle can be sufficient to generate a pattern, the pattern in general will become more accurate as information is received for additional menstrual cycles.

During the process, information can be received 408 indicating the occurrence of a menstrual cycle event for the monitored user. This can include receiving manual input from the user or data from another appropriate source, as may be detected automatically in some embodiments. This might include, for example, information about the start of a woman's period. The timing of the occurrence can be correlated 410 with the locations in the patterns of the respective metrics. As discussed, there might be one pattern generated in some embodiments that is a function of both RHR and hemoglobin concentration, or other such metrics. In some embodiments a deep neural network or other machine learning approach can be used that learns pattern based on those metrics, among other such information. Various other patterns and approaches can be used as well as discussed and suggested herein. Once the cycle event is correlated with a point in the pattern, that correlation can be used 412 to predict a timing of at least the next occurrence of the particular menstrual cycle event, as well as potentially other related cycle events as well. The pattern and correlation information is able to be updated in some embodiments any time additional cycle information is provided or obtained. Once predictions/determinations are generated or updated, those predictions can be exposed 414 to the user or another appropriate or authorized entity. The process can continue, and additional types of information can be added into the process for consideration as the information becomes available.

In some embodiments, the hemoglobin concentration in a woman's body is measured using an optical technique such as near-infrared (NIR) spectroscopy. NIR approaches can utilize an emitter 502 that emits radiation in the NIR spectrum, such as may have a wavelength in the range of 780 nm to 2500 nm. NIR has an advantage over other optical techniques in that it can penetrate the skin further than other optical techniques. Portions of the radiation that are not absorbed can be reflected back to one or more detectors 504, 506 having sensors able to detect radiation over at least the corresponding wavelength band. The absorption data determined by the detector(s) can be analyzed using a multivariate approach, such as principal component analysis (PCA) or neural networks, among other such options, to determine information about the composition of the blood in the subject's body. One or more optically dispersive elements may be used to separate out specific wavelengths for measurement. In the example 500 of FIG. 5A, two detectors are used at different positions in order to attempt to account for artifacts in the surface of the skin, as well as variations in the skin that might result from compression or other outside influences. The specific wavelength(s) used to measure hemoglobin and water concentration (e.g., near-infrared which is between 900 nm and about 1500 nm) can depend in part upon the specific implementation and design, as there can be a tradeoff between depth of penetration and sensitivity to variations in concentration, as some devices will have less sensitive detectors and some devices will be tight against the skin while some may have an amount of separation, etc. Detectors of different materials, and thus different sensitivities and accuracies, can be used as well, as may include detectors made of silicon and indium gallium arsenide, among other such options. Devices in accordance with various embodiments may also utilize more than one emitter, having different wavelengths of emission, or emitters that emit more than one wavelength, etc. In some embodiments the accuracy can depend in part upon the orientation of the device relative to the skin, the proximity to the skin, or any compression of the skin due to the device (such as by a tracker being worn tightly around the skin or being compressed by another portion of the body during sleep). Accordingly, in some embodiments a pressure sensor, camera, or other sensor can be used to attempt to account for such factors or variations.

As mentioned, in various embodiments measurements can be made primarily during periods of rest or sleep, where there will be relatively few changes in position over a period of time. Changes in hemoglobin or oxygen signals can be triggered by movements or changes in position, such that periods of rest may provide more accurate or consistent results, or representations of the true state of the body independent of many external factors. In some embodiments a device can utilize accelerometers, altimeters, inertial sensors, or other such components to monitor movement, and a tracker might want until the subject has been still (within an allowable threshold amount of movement) for at least a determined period of time of inactivity to take measurements. This can provide sufficient time for the levels to reach an equilibrium point, which can allow for greater accuracy in at least some embodiments.

As mentioned, at least some of the health data can come from other devices as well. For example, a user might be wearing a smart ring that can provide accurate heart rate information, a wrist temperature sensor that measures both skin and ambient temperature, an oral temperature sensor, or ear buds that can provide accurate body temperature information. This information can be received and then used with other available data to attempt to generate a more accurate result. For example, temperature data from earbuds alone might be used for tracking, or temperature data from earbuds, a smart ring, and a tracker can all be analyzed together, once synchronized in time, in order to remove any temperature variations that are due to external factors, as temperature readings on the wrist may be more susceptible to changes in ambient temperature, etc. The results can be averaged or otherwise collated, or if two of the three readings are consistent with variation but the third is not, then data from the third device can be removed from consideration over the time of variation, etc. Data from other external devices can be used as well within the scope of the various embodiments. For example, if data is available from blood testing machinery, urine analysis devices, etc., then other information about hormone levels or body chemistry can be used as well in predicting various cycle states and time points. Different aspects of the human body can have different patterns corresponding to the menstrual cycle, and these can be learned and applied to the available data to make as accurate a prediction as possible. As discussed, machine learning can be used as well to attempt to improve the accuracy of the pattern recognition and classifications over time. Data such as body temperature can be obtained from a number of other types of devices as well, such as may include smart clothing, bed sheets, wearables, and the like. Optical devices used to measure body characteristics, such as chemicals in the skin, through diffuse reflectance spectroscopy, photo-acoustic effects, optical coherence tomography, diffuse optical tomography, time-gated spectroscopy, or spatial frequency domain imaging can be used as well within the scope of the various embodiments.

Various algorithms and approaches can be used to analyze the data within the scope of the various embodiments. As mentioned, a first approach can obtain information from a user about her cycle. This can include approximate cycle length, as well as information about the starting and stopping times of menstruation for two or more cycles. Information about the user's body can also be obtained by a tracker or other such device that can be correlated with the cycle information. For example, resting heart rate information over those periods can be monitored to determine correlations of changes in RHR information with points in the cycle. This can include information known across various women as a base pattern, but also can be updated or determined for a specific woman to provide more accurate predictions. This can be done by advanced signal processing methods, averaging, or otherwise aggregating data obtained over additional cycles or by feeding the data into a machine learning algorithm, among other such options. The body data can be used with the cycle information to generate predictions based on the determined pattern(s). Further, as changes in the RHR information are determined over the cycle, those predictions can be updated, such as when RHR becomes indicative of a beginning of menstruation or ovulation/fertile window about to occur, etc. The predictions can be updated when the RHR indicates that a menstrual cycle event has ended.

Users can be clustered according to common characteristics such as location, genetic history, or other characteristics. The system can then create models that are specific to each cluster. This can provide more accurate results unique to a cluster. For example, one cluster may have higher normal resting heart rates and if a user in that cluster was given a generic model, her results might be inaccurate.

Other or additional types of body data can be used as well as discussed herein. The data can be provided as inputs to a modeling or machine learning process that can use the information to predict information for at least the current or next cycle. As mentioned, there may be various body data inputs, as may relate to heart rate, hemoglobin concentration, and others discussed herein. Pattern and cycle correlation information can be determined and used for each available type of data to attempt to come to a more accurate determination. The data values may be weighted by different amounts, such as may be based upon strength of prediction or accuracy, among other such factors. These weightings can be updated or modified over time, such as may be based upon machine learning or changes in a woman's body or state, etc. There may also be different confidence levels or other factors that can impact the relative weightings as well. The weight values chosen can also depend on the signal-to-noise ration of some signals. Menstrual cycle event prediction can be associated with a relative percentage of accuracy. For example, a level of confidence for fertile window prediction can be determined. In addition or alternative to determining a binary value for the fertile window (true or false), such a level of confidence can be useful to a user who is trying to conceive or is avoiding conception as she can determine how likely she is within a fertile window.

As mentioned, various other types of information can be utilized as well that may impact the timing of a cycle or relevance of different body data values. For example, information may be obtained about the amount of exercise or physical activity a person has undergone during a given day or period, which may account for differences in detected body data values as discussed herein. There may also be variations in diet, stress, weight, body fat percentage, body mass index (BMI), medication, or other such factors that can be accounted for as well. In at least some embodiments these and other such factors can be fed into a predictive model and then a regression applied in order to verify conditions for accurate predictions, etc.

As discussed, the cycle information can be surfaced in a number of different ways. There can be various options through which a user can navigate, or there can be specific interfaces or displays provided, among other such options. For example, an application might provide a countdown until an upcoming period, or a calendar view that lists predicted days of ovulation, fertile window, and menstruation. In some embodiments the symptoms of various users can be determined and the application can begin to predict when those users will suffer cramps, acne, headaches, tender breasts, poor sleep quality or durations, etc. The application might also provide different views depending upon a user's goals, such as a different view if the user is attempting to conceive versus not conceive. In some embodiments the application might also provide recommendations for improving health or achieving the goal, based at least in part upon the monitored health information. Recommendations can also be made to see a doctor in cases where the body data might indicate a potential medical condition. As an example, for primary and secondary Dysmenorrhea the underlying physiological reasons seem to be different and one of the symptoms of secondary versus primary dysmenorrhea is the fact that cramps are suffered all throughout the cycle (for primary dysmenhorrea, or the common female population, cramps tend to be worst in the first days of the period). The data gathered and analyzed can then be used as a tool for diagnosis.

In at least some embodiments the recommendations or weightings may change over time, such as for changes in the body or exercise levels, age, and the like. Additional information may be captured as well, such as may relate to flow or cramping, which can be correlated to various body metrics. This can then be used to predict similar symptoms for a current or upcoming cycle.

As mentioned, the various embodiments can be implemented as a system that includes one or more tracking devices for a given user. In other embodiments the embodiments may be provided as a service, which users can utilize for their devices. Other tracker providers may also subscribe or utilize such a service for their customers. In some embodiments an application programming interface (API) or other such interface may be exposed that enables collected body data, and other information, to be received to the service, which can process the information and send the results back down to the tracker, or related computing device, for access by the user. In some embodiments at least some of the processing may be done on the tracking or computing device itself, but processing by a remote system or service may allow for more robust processing, particularly for tracking devices with limited capacity or processing capability.

Figure 6:
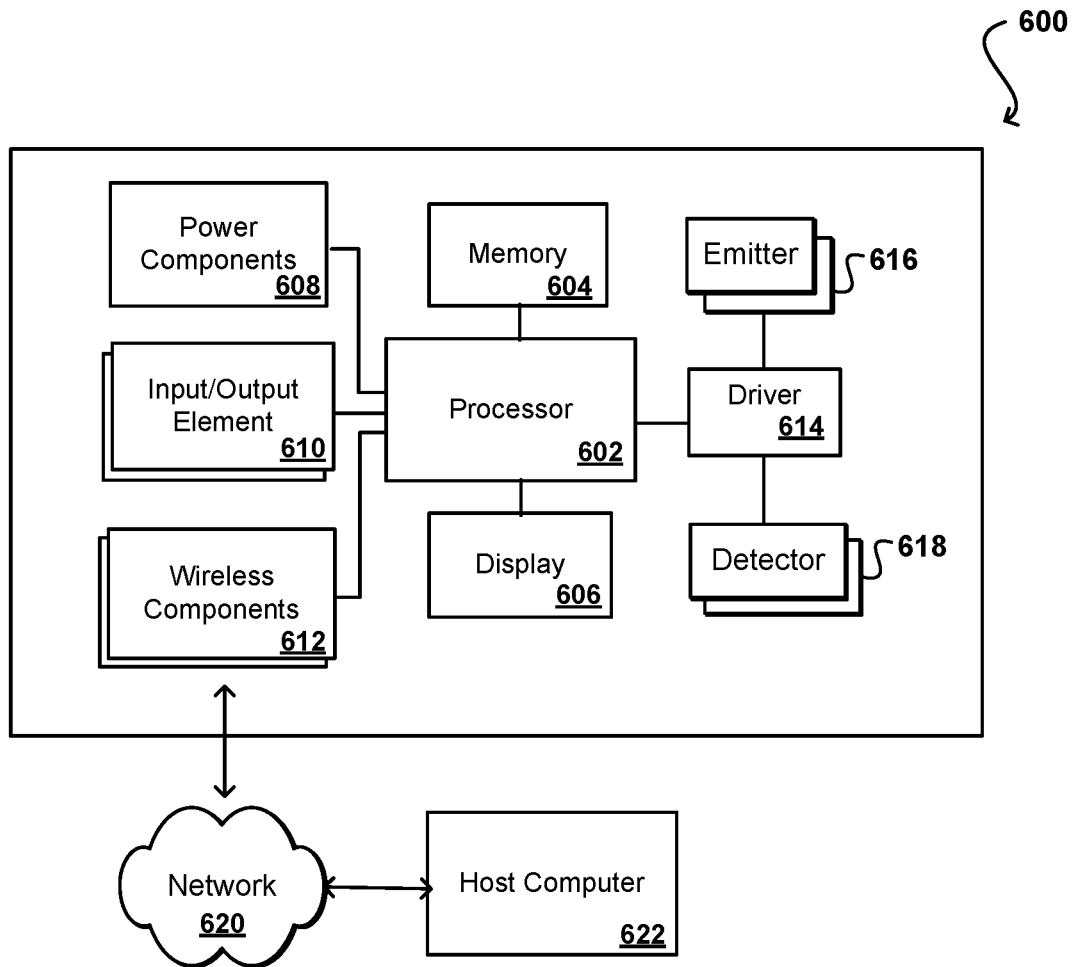
FIG. 6 illustrates components of an example device that can be utilized in accordance with various embodiments.

FIG. 6 illustrates components of an example cycle prediction system 600 that can be utilized in accordance with various embodiments. In this example, the device includes at least one processor 602, such as a central processing unit (CPU) or graphics processing unit (GPU) for executing instructions that can be stored in a memory device 604, such as may include flash memory or DRAM, among other such options. As would be apparent to one of ordinary skill in the art, the device can include many types of memory, data storage, or computer-readable media, such as data storage for program instructions for execution by a processor. The same or separate storage can be used for images or data, a removable memory can be available for sharing information with other devices, and any number of communication approaches can be available for sharing with other devices. The device typically will include some type of display 606, such as a touch screen, organic light emitting diode (OLED), or liquid crystal display (LCD), although devices might convey information via other means, such as through audio speakers or projectors.

A tracker or similar device will include at least one motion detection sensor, which as illustrated can include at least one I/O element 610 of the device. Such a sensor can determine and/or detect orientation and/or movement of the device. Such an element can include, for example, an accelerometer, inertial sensor, altimeter, or gyroscope operable to detect movement (e.g., rotational movement, angular displacement, tilt, position, orientation, motion along a non-linear path, etc.) of the device. An orientation determining element can also include an electronic or digital compass, which can indicate a direction (e.g., north or south) in which the device is determined to be pointing (e.g., with respect to a primary axis or other such aspect). A device may also include an I/O element 610 for determining a location of the device (or the user of the device). Such a positioning element can include or comprise a GPS or similar location-determining element(s) operable to determine relative coordinates for a position of the device. Positioning elements may include wireless access points, base stations, etc., that may either broadcast location information or enable triangulation of signals to determine the location of the device. Other positioning elements may include QR codes, barcodes, RFID tags, NFC tags, etc., that enable the device to detect and receive location information or identifiers that enable the device to obtain the location information (e.g., by mapping the identifiers to a corresponding location). Various embodiments can include one or more such elements in any appropriate combination. The I/O elements may also include one or more biometric sensors, optical sensors, barometric sensors (e.g., altimeter, etc.), and the like.

As mentioned above, some embodiments use the element(s) to track the location and/or motion of a user. Upon determining an initial position of a device (e.g., using GPS), the device of some embodiments may keep track of the location of the device by using the element(s), or in some instances, by using the orientation determining element(s) as mentioned above, or a combination thereof. As should be understood, the algorithms or mechanisms used for determining a position and/or orientation can depend at least in part upon the selection of elements available to the device. The example device also includes one or more wireless components 612 operable to communicate with one or more electronic devices within a communication range of the particular wireless channel. The wireless channel can be any appropriate channel used to enable devices to communicate wirelessly, such as Bluetooth, cellular, NFC, or Wi-Fi channels. It should be understood that the device can have one or more conventional wired communications connections as known in the art. The device also includes one or more power components 608, such as may include a battery operable to be recharged through conventional plug-in approaches, or through other approaches such as capacitive charging through proximity with a power mat or other such device. In some embodiments the device can include at least one additional input/output device 610 able to receive conventional input from a user. This conventional input can include, for example, a push button, touch pad, touch screen, wheel, joystick, keyboard, mouse, keypad, or any other such device or element whereby a user can input a command to the device. These I/O devices could even be connected by a wireless infrared or Bluetooth or other link as well in some embodiments. Some devices also can include a microphone or other audio capture element that accepts voice or other audio commands. For example, a device might not include any buttons at all, but might be controlled only through a combination of visual and audio commands, such that a user can control the device without having to be in contact with the device.

As mentioned, many embodiments will include at least some combination of one or more emitters 616 and one or more detectors 618 for measuring data for one or more metrics of a human body, such as for a person wearing the tracker device. In some embodiments this may involve at least one imaging element, such as one or more cameras that are able to capture images of the surrounding environment and that are able to image a user, people, or objects in the vicinity of the device. The image capture element can include any appropriate technology, such as a CCD image capture element having a sufficient resolution, focal range, and viewable area to capture an image of the user when the user is operating the device. Methods for capturing images using a camera element with a computing device are well known in the art and will not be discussed herein in detail. It should be understood that image capture can be performed using a single image, multiple images, periodic imaging, continuous image capturing, image streaming, etc. Further, a device can include the ability to start and/or stop image capture, such as when receiving a command from a user, application, or other device.

The example device in FIG. 6 includes emitters 616 and detectors 618 capable of being used for obtaining optical photoplethsymogram (PPG) measurements. Some PPG technologies rely on detecting light at a single spatial location, or adding signals taken from two or more spatial locations. Both of these approaches result in a single spatial measurement from which the heart rate (HR) estimate (or other physiological metrics) can be determined. In some embodiments, a PPG device employs a single light source coupled to a single detector (i.e., a single light path). Alternatively, a PPG device may employ multiple light sources coupled to a single detector or multiple detectors (i.e., two or more light paths). In other embodiments, a PPG device employs multiple detectors coupled to a single light source or multiple light sources (i.e., two or more light paths). In some cases, the light source(s) may be configured to emit one or more of green, red, and/or infrared light. For example, a PPG device may employ a single light source and two or more light detectors each configured to detect a specific wavelength or wavelength range. In some cases, each detector is configured to detect a different wavelength or wavelength range from one another. In other cases, two or more detectors configured to detect the same wavelength or wavelength range. In yet another case, one or more detectors configured to detect a specific wavelength or wavelength range different from one or more other detectors). In embodiments employing multiple light paths, the PPG device may determine an average of the signals resulting from the multiple light paths before determining an HR estimate or other physiological metrics. Such a PPG device may not be able to resolve individual light paths or separately utilize the individual signals resulting from the multiple light paths.

Figure 7:
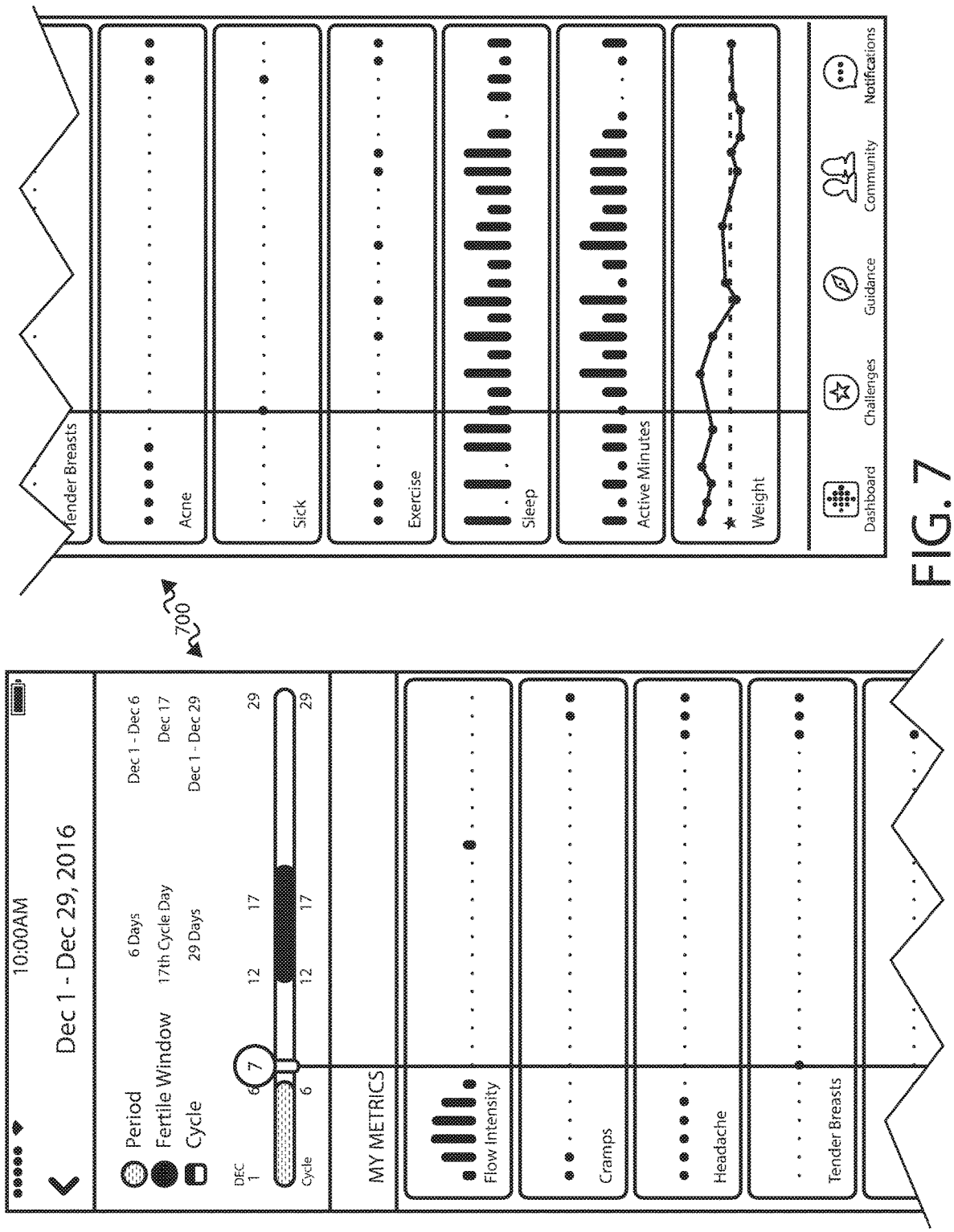
FIG. 7 illustrates an example user interface that can be utilized in accordance with various embodiments.
Figure 8:
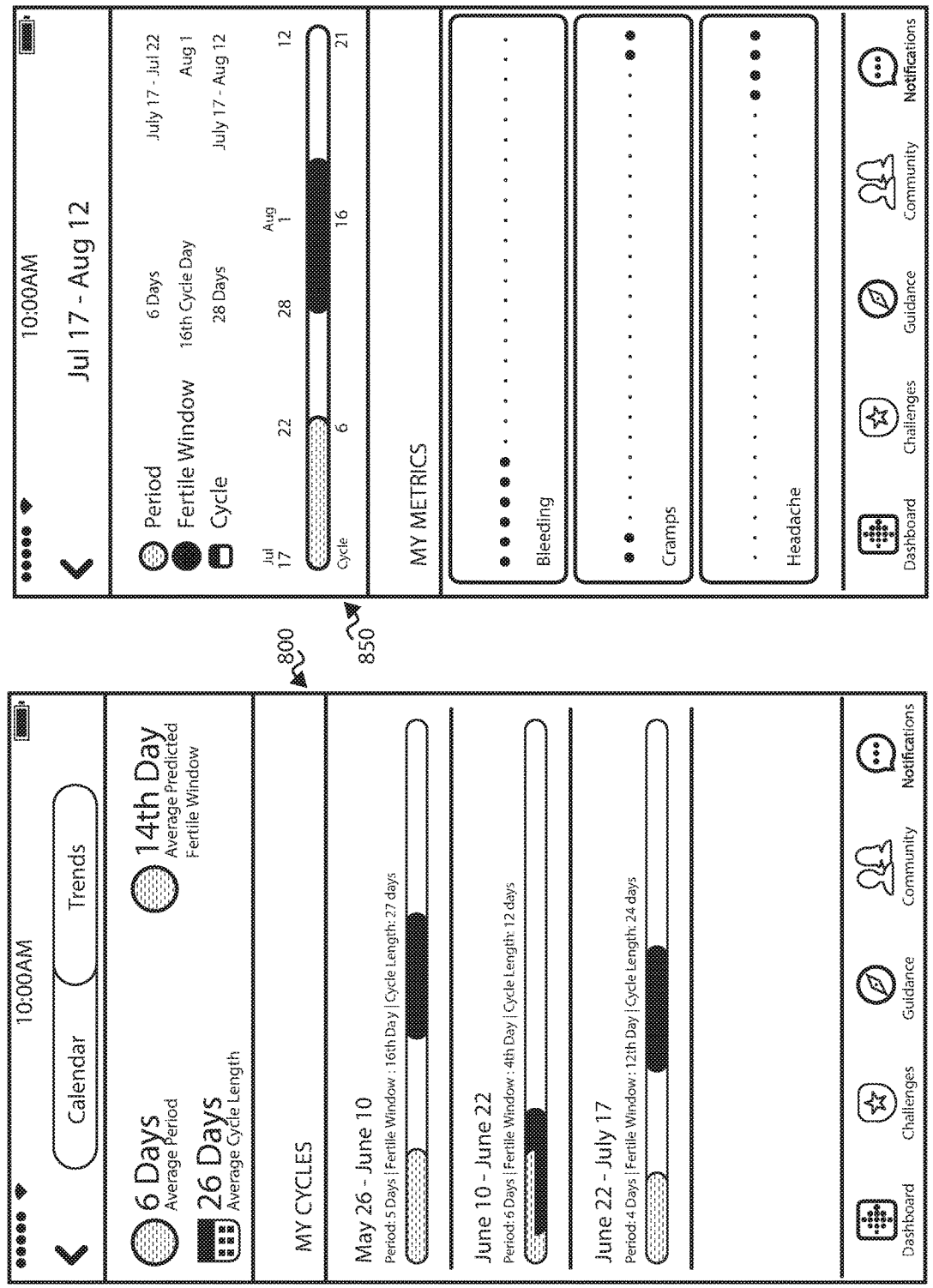
FIG. 8 illustrates an example user interface that can be utilized in accordance with various embodiments.
Figure 9:
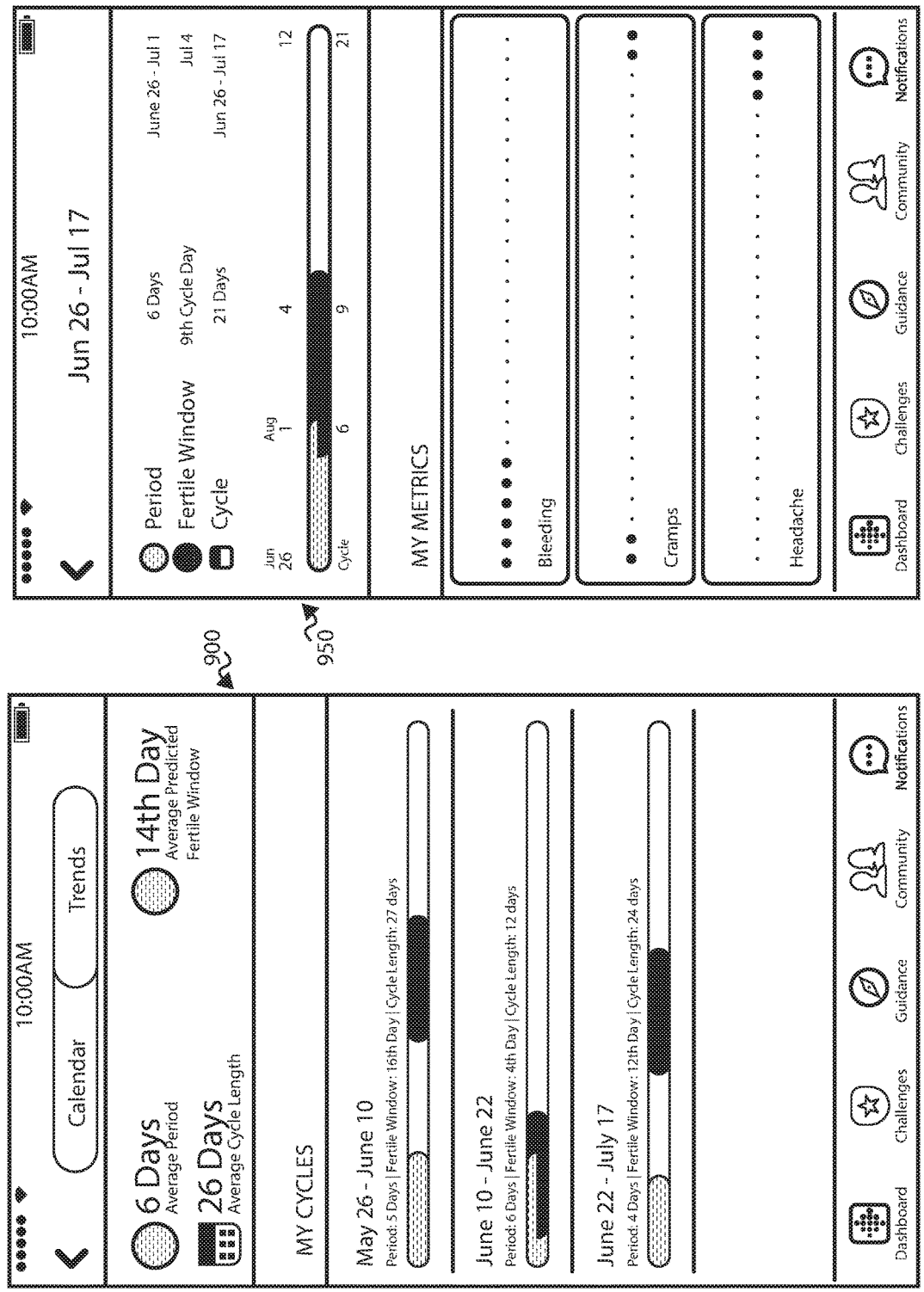
FIG. 9 illustrates an example user interface that can be utilized in accordance with various embodiments.

FIGS. 7-9 illustrate example user interfaces that can be utilized in accordance with various embodiments, wherein various metrics discussed herein can be visually correlated for the user. For example, FIG. 7 illustrates an interface 700 that provides various metrics that are determined for a user over a given menstrual cycle. In addition to provide timing information for the period, ovulation, and overall menstrual cycle, the interface illustrates days during the cycle in which cramping or acne were detected, breasts were tender, etc. This can be provided for each cycle, and available historically for comparison. Other information can be displayed as well, such as relate to periods of exercise, weight fluctuation, sleep patterns, and the like. The bar across the top enables the user to zoom or focus on specific days in the cycle. The top circles show whichever day the user has scrubbed to, allowing them to explore without having to show all the day numbers at once. On a touch and hold, a vertical visual alignment assist ruler can appear to help with the analysis.

FIG. 8 illustrates a pair of interface pages 800, 850 that can be provided in accordance with various embodiments. In the first interface page 800, a user can view information about different cycles, and can obtain information about trends in the cycles. A user can then select any of these cycles to obtain the second interface page 850 which displays information for that cycle similar to that described with respect to FIG. 7. Such an interface enables a user to quickly view information for cycles that may have been atypical, for example, and see how that impacted various symptoms, such as whether an atypical menstrual cycle was associated with more headaches or cramping. The amount of information can be controlled in some aspects through scrolling, such as where a user can scroll up to hide the summary section, and further scrolling can scroll the metrics behind the header, among other such options. FIG. 9 illustrates a similar pair of interface pages 900, 950, except that in this example there is overlap between the period and the time for ovulation. The overlap is shown graphically so that the user can better understand what is happening with their body, and how this correlates with various symptoms they experience.

In some embodiments a user wearing the PPG device might perform an activity involving motion (or contorting of the wrist, for example, for a wrist-worn PPG device, thereby affecting the dynamics of the blood flow within the wrist). In such instances the accuracy of the HR estimate provided by the PPG device may be reduced or compromised. The light intensity received by the light detectors may be modulated by these movements typically at an order of magnitude or greater than the desired cardiac signal. Therefore, a preprocessing step where the signal effect of these movements is removed can be utilized to improve HR estimation accuracy during motion. In addition to the deleterious effects of motion, another cause of reduced signal quality in PPG devices may be the characteristics of the local area being sensed. For instance, signal quality can vary dramatically if a wrist-worn PPG sensor is moved only a few millimeters up or down the wrist. In addition, during motion, certain portions of the wrist-worn PPG devices may be subject to more motion depending on their location, position, and/or orientation, and PPG sensors placed on such portions may therefore result in greater degradation of the PPG signal due to motion.

Various embodiments enable a PPG device to utilize signals based on two or more independently addressable source-detector combinations such that the signal quality of the PPG device is improved, especially during activities involving motion. In some embodiments, PPG signals can be acquired via multiple light paths involving one or more sources and one or more detectors placed at different spatial locations. These multiple PPG signals can then be processed to isolate the cardiac component (e.g., by removing the motion component) from the PPG signals. For example, the motion component may be removed based on inputs from the accelerometer, unsupervised learning and/or previously done supervised learning. Additionally, or alternatively, the PPG signals corresponding to these multiple light paths are compared using a quality metric such that the highest-quality PPG signal can be selected to be used for estimating HR or other physiological metrics, as well as sleep time of or other potential aspects.

In order to utilize two or more source-detector pairs for motion signal rejection, a PPG device in accordance with various embodiments can use a computer program to identify the motion component of a given signal and remove the motion component from the composite signal, leaving only the cardiac signal as a remainder. In some implementations, the temporal phase of the cardiac waveform is assumed to stay constant between different light paths, while the phase of the motion signal is expected to vary between light paths due to how the PPG sensor interacts with the skin surface during activities involving motion (e.g., pressure at the PPG/skin interface may vary depending on the spatial location of the light source and the light detector of the light path). Using this concept, PPG devices can fit mathematical models to the spatial light path signals to identify the cardiac and motion components. First, PPG signals are extracted by each source-detector combination. For example, two light sources and two light detectors would result in four source-detector combinations. A mathematical model can then be fit to the different spatial points, from which characteristic signals are extracted related to the cardiac and motion components of the PPG signals. PPG devices may also implement other techniques including, but not limited to, independent component analysis (ICA) and other forms of blind source separation.

Although some embodiments are described with reference to HR or cardiac components of PPG signals, the techniques described herein may be extended to other types of physiological metrics described herein, such as may relate to $SpO_2$, or other types of signals that can be extracted from the PPG signals to determine such physiological metrics. For example, in some embodiments, a method for determining an $SpO_2$ value comprises receiving a first set of one or more PPG signals from one or more PPG sensors, which may include analog signals or digital data sampled from analog components and stored in computer memory. The first set of PPG signals may correspond to red and/or infrared light previously emitted by one or more emitters after the emitted light has interacted with the user's skin, when the monitoring device is worn by the user. A first set of PPG signals may include a noise component. The method for determining the $SpO_2$ value may further comprise receiving a second set of one or more PPG signals from the one or more PPG sensors or detectors, which may include analog signals or digital data sampled from analog components and stored in computer memory. For example, the second set of PPG signals may be obtained from different ranges of wavelengths emitted from the light source than the first set of PPG signals. For example, the second set of PPG signals may be obtained from one or more green light sources. In some cases, the second set of PPG signals is obtained from a system within the device used for tracking a user's heart rate. In other cases, the second set of PPG signals is received from a system separate from HR detection. The method for determining the $SpO_2$ value may further comprise filtering the first set of PPG signals based on a feature of the second set of PPG signals to generate a filtered set of PPG signals. Various filtering techniques may be used to remove noise or other features from the first set of PPG signals based on a feature of the second set of PPG signals. As one example, HR may be the feature of the second set of PPG signals. In the case of HR, the device may create a filter based at least in part upon the detected frequency of the HR signal. Examples of filters include a low-pass filter, a high-pass filter, and a narrow band filter that excludes frequencies that are inconsistent with the frequency of the HR signal. The method for determining the $SpO_2$ value may further comprise using one range of wavelengths to better measure an underlying signal on which the wavelengths of the first set of PPG signals operates. Based on this underlying signal (or features derived therefrom), the device can improve the first set of PPG signals based on filtering noise from the first set of PPG signals. Further, the filtered set of PPG signals can be used to create and store a $SpO_2$ value. As an example, the filtered set of PPG signals may have a reduced or eliminated noise component and therefore may serve as a more accurate basis for creating and storing the $SpO_2$ value.

In some embodiments, an intermediate HR estimation can be performed based on PPG signals from two or more light paths. For each of the acquired PPG signals, the PPG device may determine an estimate of the HR in beats-per-minute (BPM) and compute a confidence metric associated with the PPG signal, which is indicative of the signal quality for the particular light path associated with the PPG signal. It may also be possible to compute a confidence metric without an intermediate HR estimation, for example by characterizing characteristics (e.g., statistics) of the PPG signal or filtered versions of the PPG signal. In some embodiments, each confidence metric corresponds to a single PPG signal. In other cases, each confidence metric corresponds to multiple PPG signals. For example, a confidence metric may be computed for each way of combining the PPG signals (e.g., signals A+B, signals A+C, signals B+C, signals A+B+C, etc.), as well as for various combinations of PPG signals (e.g., selecting at least two of signals A, B, and C). In other cases, one confidence metric corresponds to a single PPG signal and another confidence metric corresponds to a combination of multiple PPG signals. The PPG device can select an HR estimate from the multiple HR estimates corresponding to the multiple light paths (e.g., by selecting the HR estimate of the PPG signal having the highest confidence metric). Alternatively, the PPG device may assign different weight values to the multiple HR estimates based on the confidence metric values associated with the individual and/or multiple PPG signals and compute a final HR estimate based on the weight values. The confidence values and/or the weight values may be updated or optimized using unsupervised machine learning. The PPG device may implement hysteresis logic which prevents jumping between light paths in a short time window if the confidence metric values corresponding to the two light paths are within a threshold value. The PPG device may also implement logic configured to bias the selection of HR estimates based on user data, activity data, movement data, or other data accessible by the PPG device. The PPG device may apply a smoothing filter on the HR estimates, for example, to improve accuracy and provide a better user experience.

One advantage of such an approach lies in the fact that the spatial information associated with the light sources and/or light detectors can be used by different algorithms to improve HR or other physiological metric estimation accuracy of the PPG sensing device, especially when the user of the device is exercising or performing activities involving motion. Existing implementations typically rely on algorithms to improve the HR or other physiological metric estimation performance, but do not have the benefit of the extra sensor data generated based on multiple light paths.

Figure 5:
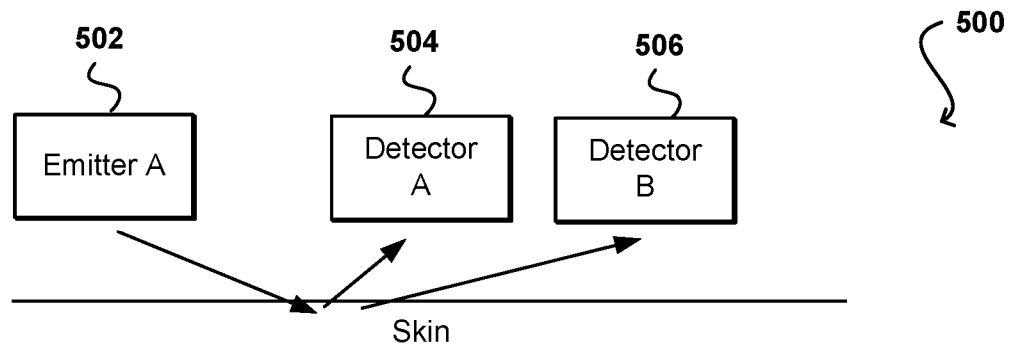
FIG. 5 illustrates example light paths that can be utilized in accordance with various embodiments.

As discussed with respect to the situation 500 of FIG. 5, light emitted from one or more emitters 502 can be reflected from the skin back to the detectors 504, 506. Although a user in various embodiments would wear a tracker or other PPG device proximate a wrist location, in other embodiments such a device may be worn in locations such as the ear, fingertips, ankle, neck, upper arm, torso, leg and/or forehead (e.g., such that light sources of the PPG devices are adjacent to blood vessels of a human).

The path light travels from an emitter 502 to the skin and back to one of the detectors 504, 506 shall be referred to herein as a light path. In addition to having its ordinary meaning, a light path can refer to the probabilistic path of photons from one location to another, typically from the light source (or emitter) to the light sensor (or detector). Photons emitted by the emitter will follow many different paths to each detector. For simplicity and clarity, the path that results from the optical power-weighted average of all the possible paths is described simply as the "light path" in some embodiments. In some alternative embodiments, "light path" refers to the path along which most of the photons travel. In yet other embodiments, "light path" refers to an approximated vector having an origin at a center of a light source and terminating anywhere in the surface area of a detector, and representing an approximate path of light from the source to the detector.

A light path represents an approximate path of light from a given source to a given detector. Thus, for example, if there are multiple sources and multiple detectors, then a distinct light path exist between each of the multiple sources and each of the multiple detectors. Thus, consistent with the embodiments described herein, PPG signals associated with any of the aforementioned light paths may be selectively obtained and utilized for estimating HR and/or other physiological metrics. For example, the PPG signals corresponding to any of multiple paths may be compared using a quality/confidence metric such as a signal-to-noise ratio (SNR), and the PPG signal having the highest quality can be selected to be used for estimating the HR and/or other physiological metrics.

Referring back to FIG. 6, an example PPG device may further comprise one or more processors 602 coupled to memory 604, a display 606, a bus, one or more input/output (I/O) elements 610, and wireless networking components 612, among other such options. A display and/or I/O devices may be omitted in certain embodiments. If included, a display 606 may provide an interface for displaying data, such as HR, blood oxygen saturation ($SpO_2$) levels, and other metrics of the user. For example, the processor 602 may compute values for the physiological metrics monitored by the PPG device based on one or more PPG signals generated by the light detectors 618. In an embodiment, the PPG device is a wristband and the display is configured such that the display faces away from the outside of a user's wrist when the user wears the PPG device. In other embodiments, the display may be omitted and data detected by the PPG device may be transmitted using the wireless networking interface via near-field communication (NFC), Bluetooth, Wi-Fi, or other suitable wireless communication protocols over at least one network 620 to a host computer 622 for analysis, display, reporting, or other such use.

The memory 604 may comprise RAM, ROM, FLASH memory, or other non-transitory digital data storage, and may include a control program comprising sequences of instructions which, when loaded from the memory and executed using the processor 602, cause the processor 602 to perform the functions that are described herein. The emitters 616 and detectors 618 may be coupled to a bus directly or indirectly using driver circuitry by which the processor 602 may drive the light emitters 616 and obtain signals from the light detectors 618. The host computer 622 communicate with the wireless networking components 612 via one or more networks 620, which may include one or more local area networks, wide area networks, and/or internetworks using any of terrestrial or satellite links. In some embodiments, the host computer 622 executes control programs and/or application programs that are configured to perform some of the functions described herein.

In some embodiments, each emitter 616 can be individually controlled, or each light detector 618 can be individually read out when multiple detectors are used, and in such embodiments, PPG sensor data along several different light paths can be collected. The control program can utilize the collected data to provide a more accurate estimation or HR and/or other physiological metrics. In related aspects, the processor 602 and other component(s) of the PPG device may be implemented as a System-on-Chip (SoC) that may include one or more central processing unit (CPU) cores that use one or more reduced instruction set computing (RISC) instruction sets, and/or other software and hardware to support the PPG device.

In various embodiments, the emitters (or light sources) comprise electronic semiconductor light sources, such as LEDs, or produce light using any of filaments, phosphors, or laser. In some implementations, each of the light sources emits light having the same center wavelength or within the same wavelength range. In other cases, at least one light source may emit light having a center wavelength that is different from another one of the light sources. The center wavelengths of the light emitted by the light sources may be in the range of 495 nm to 570 nm. For example, a particular green light source may emit light with a center wavelength of 528 nm. In other embodiments, one or more of the light sources may emit red light (e.g., 660 nm center wavelength) or IR light (e.g., 940 nm center wavelength). In some embodiments, one or more of the light sources may emit light with peak wavelengths typically in the range of 650 nm to 940 nm. For example, in various embodiments, a particular red light source may emit light with a peak wavelength of 660 nm, and one or more infrared light sources may emit light with peak wavelengths in the range of 750 nm to 1700 nm. By way of example and not limitation, a particular infrared light source may emit light with a peak wavelength of 730 nm, 760 nm, 850 nm, 870 nm, or 940 nm. In some cases, commercial light sources such as LEDs may provide output at about 20 nm intervals with a center wavelength tolerance of +/−10 nm from the manufacturer's specified wavelength and thus one possible range of useful peak wavelengths for the light sources is 650 nm to 950 nm. The green light sources may be configured to emit light with wavelengths in the range of 495 nm to 570 nm. For example, a particular green light source may emit light with a wavelength of 528 nm. The green light sources may be equally spaced from light detectors as the pairs of red and infrared light sources. For example, if the distance between light detectors and a center of a first red light source is 2 mm, the distance between light detectors and a green light source may also be 2 mm (e.g., equidistant). In some other cases, the distance between the light detectors and one or more light sources is not equidistant. Further, in some embodiments, one or more of the light sources may comprise a single LED package that emits multiple wavelengths, such as green, red and infrared wavelengths, at the same or substantially the same (e.g., less than 1 mm difference) location with respect to multiple detectors. Such LEDs may include multiple semiconductor elements co-located using a single die in a single package.

The spacing of the light sources may be measured from the side of the light source or the center of the light source. For example, the light sources may be configured such that the center of each light source is at a first distance from the edge of the closest one of the light detectors. In some embodiments, the first distance may be 2 mm. In some implementations, each light source is located at a second distance from the closest one of the light sources, and each light detector is located at a third distance from the closest one of the light detectors. In some embodiments, the second and third distances are identical to the first distance. In other embodiments, each of the second and third distances is different from the first distance. The second distance may be identical to or different from the third distance. The particular magnitude of the spacing may depend on a number of factors and this disclosure does not limit the embodiments to any particular spacing. For example, spacing in a range of 1 mm (or less) to 10 mm would be workable in various embodiments.

In some embodiments, independent control of all light sources is provided. In other embodiments, several light sources are controlled together as a gang or bank. A benefit of independent control of each light source, or independent readout from each of multiple detectors (e.g., obtaining independent signals based on the same or different light wavelengths from each of multiple detectors), is that a multiple light path approach may be used to improve the estimation of HR and/or other physiological metrics, as discussed further herein.

Light detectors may comprise one or more sensors that are adapted to detect wavelengths of light emitted from the light sources. A particular light source combined with a particular detector may comprise a sensor such as a PPG sensor. A first PPG sensor and a second PPG sensor can share components, such as the same light sources and/or detectors, or have different components and thus the term "PPG sensor," in addition to having its ordinary meaning, may refer to any of such arrangements although actual embodiments may use multiple components in implementing a PPG sensor. The term "PPG device," in addition to having its ordinary meaning, may refer to a device including a PPG sensor. A light detector, in an embodiment, may comprise one or more detectors for detecting each different wavelength of light that is used by the light sources. For example, a first detector may be configured to detect light with a wavelength of 560 nm, a second detector may be configured to detect light with a wavelength of 940 nm, and a third detector may be configured to detect light with a wavelength of 528 nm. Examples include photodiodes fabricated from semiconductor materials and having optical filters that admit only light of a particular wavelength or range of wavelengths. The light detectors may comprise any of a photodiode, phototransistor, charge-coupled device (CCD), thermopile detector, microbolometer, or complementary metal-oxide-semiconductor (CMOS) sensor. The light detectors may comprise multiple detector elements, as further described herein. One or more of the detectors may comprise a bandpass filter circuit.

In other embodiments, a detector may comprise one or more detectors configured to detect multiple wavelengths of light. For example, a single detector may be configured to tune to different frequencies based on data received from an electrical digital microprocessor coupled to detectors. In another way, the single detector may include multiple active areas where each active area is sensitive to a given range of wavelengths. In an embodiment, a single detector is configured to detect light with wavelengths in the red and IR frequencies and a second detector is configured to detect light with wavelengths in the green frequencies. Further, each of the light sources may use any of one or more different wavelengths of light as previously described.

In an embodiment, light detectors can be mounted in a housing with one or more filters that are configured to filter out wavelengths of light other than wavelengths emitted by light sources. For example, a portion of the housing may be covered with a filter which removes ambient light other than light in wavelengths emitted by light sources. For example, signals from light sources may be received at the light detectors through an ambient light filter that filters out an ambient light source that generates an ambient light with a wavelength that is different from the wavelength that is detected by the detector. Although LEDs and photodiodes are used as examples of the light sources and the light detectors, respectively, the techniques described herein may be extended to other types of light sources. For example, edge emitting lasers, surface emitting lasers, LED-pumped phosphors that generate broadband light. The techniques described herein may be extended to other combinations of light sources and detectors. For example, the PPG device may include (i) single or multiple LEDs and a multi-element photodetector (e.g., a camera sensor), (ii) an LED array and single or multiple photodiodes, (iii) a broadband LED-pumped phosphor and detector array with wavelength selective filters on each detector, (iv) spatial light modulator (SLM) (e.g., a digital micromirror device [DMD] or a liquid crystal on silicon [LCoS] device) and single or multiple LEDs, other combinations thereof, or other configurations of light sources and detectors.

Certain flow diagrams are presented herein to illustrate various methods that may be performed by example embodiments. The flow diagrams illustrate example algorithms that may be programmed, using any suitable programming environment or language, to create machine code capable of execution by a CPU or microcontroller of the PPG device. In other words, the flow diagrams, together with the written description in this document, are disclosures of algorithms for aspects of the claimed subject matter, presented at the same level of detail that is normally used for communication of this subject matter among skilled persons in the art to which the disclosure pertains. Various embodiments may be coded using assembly, C, OBJECTIVE-C, C++, JAVA, or other human-readable languages and then compiled, assembled, or otherwise transformed into machine code that can be loaded into ROM, EPROM, or other recordable memory of the activity monitoring apparatus that is coupled to the CPU or microcontroller and then then executed by the CPU or microcontroller.

In an embodiment, PPG signals obtained from multiple light paths may be processed to filter or reject signal components that are associated with motion of the user, using a computer program to identify the motion component of the signal and remove the identified motion component from the composite signal, leaving the cardiac component as a remainder or final signal.

In an embodiment, PPG signals might be collected in variety of activities during day or at night, such as may relate to periods of walking, exercise, or sleep. Other on-device sensors including an accelerometer, gyroscope, or altimeter may be used to categorize or detect the activity, or human posture as a basis to develop the appropriate filters. These filters or signal processing methods might be used for targeted reduction of variability in the PPG data with multiple light paths. As an example and not limitation, the accelerometer data can be used to develop signal processing methods to filter the PPG data and look into a certain posture, removing other body orientations. This can help reduce the noise in the PPG data and get a better assessment of the corresponding physiological variables for the corresponding light paths.

In various embodiments, approaches discussed herein may be performed by one or more of: firmware operating on a monitoring or tracker device or a secondary device, such as a mobile device paired to the monitoring device, a server, host computer, and the like. For example, the monitoring device may execute operations relating to generating signals that are uploaded or otherwise communicated to a server that performs operations for removing the motion components and creating a final estimate value for HR, $SpO_2$, and/or other physiological metrics. Alternatively, the monitoring device may execute operations relating to generating the monitoring signals and removing the motion components to produce a final estimate value for HR, $SpO_2$, and/or other physiological metrics local to the monitoring device. In this case, the final estimate may be uploaded or otherwise communicated to a server such as host computer that performs other operations using the value.

An example monitoring or tracker device can collect one or more types of physiological and/or environmental data from one or more sensor(s) and/or external devices and communicate or relay such information to other devices (e.g., host computer or another server), thus permitting the collected data to be viewed, for example, using a web browser or network-based application. For example, while being worn by the user, a tracker device may perform biometric monitoring via calculating and storing the user's step count using one or more sensor(s). The tracker device may transmit data representative of the user's step count to an account on a web service (e.g., www.fitbit.com), computer, mobile phone, and/or health station where the data may be stored, processed, and/or visualized by the user. The tracker device may measure or calculate other physiological metric(s) in addition to, or in place of, the user's step count. Such physiological metric(s) may include, but are not limited to: energy expenditure, e.g., calorie burn; floors climbed and/or descended; HR; heartbeat waveform; HR variability; HR recovery; respiration, $SpO_2$, blood volume, blood glucose, skin moisture and skin pigmentation level, location and/or heading (e.g., via a GPS, global navigation satellite system (GLONASS), or a similar system);

elevation; ambulatory speed and/or distance traveled; swimming lap count; swimming stroke type and count detected; bicycle distance and/or speed; blood glucose; skin conduction; skin and/or body temperature; muscle state measured via electromyography; brain activity as measured by electroencephalography; weight; body fat; caloric intake; nutritional intake from food; medication intake; sleep periods (e.g., clock time, sleep phases, sleep quality and/or duration); pH levels; hydration levels; respiration rate; and/or other physiological metrics.

An example tracker or monitoring device may also measure or calculate metrics related to the environment around the user (e.g., with one or more environmental sensor(s)), such as, for example, barometric pressure, weather conditions (e.g., temperature, humidity, pollen count, air quality, rain/snow conditions, wind speed), light exposure (e.g., ambient light, ultra-violet (UV) light exposure, time and/or duration spent in darkness), noise exposure, radiation exposure, and/or magnetic field. Furthermore, a tracker device (and/or the host computer and/or another server) may collect data from one or more sensors of the device, and may calculate metrics derived from such data. For example, a tracker device may calculate the user's stress or relaxation levels based on a combination of HR variability, skin conduction, noise pollution, and/or sleep quality. In another example, a tracker device may determine the efficacy of a medical intervention, for example, medication, based on a combination of data relating to medication intake, sleep, and/or activity. In yet another example, a tracker device may determine the efficacy of an allergy medication based on a combination of data relating to pollen levels, medication intake, sleep and/or activity. These examples are provided for illustration only and are not intended to be limiting or exhaustive.

An example monitoring device may include a computer-readable storage media reader, a communications device (e.g., a modem, a network card (wireless or wired), an infrared communication device) and working memory as described above. The computer-readable storage media reader can be connected with, or configured to receive, a computer-readable storage medium representing remote, local, fixed and/or removable storage devices as well as storage media for temporarily and/or more permanently containing, storing, transmitting and retrieving computer-readable information. A monitoring system and various devices also typically will include a number of software applications, modules, services or other elements located within at least one working memory device, including an operating system and application programs such as a client application or Web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Storage media and other non-transitory computer readable media for containing code, or portions of code, can include any appropriate media known or used in the art, such as but not limited to volatile and non-volatile, removable and non-removable media implemented in any method or technology for storage of information such as computer readable instructions, data structures, program modules or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices or any other medium which can be used to store the desired information and which can be accessed by a system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

What is claimed is:

1. A system, comprising:
   a display device;
   a monitoring device including a non-invasive measurement sub-system;
   at least one processor; and
   memory including instructions that, when executed by the at least one processor, cause the monitoring device to:
      obtain historical user information for one or more events related to a menstrual cycle of a user;
      generate a prediction for a future event related to the menstrual cycle, the prediction based at least in part on the historical user information as input into a predictive model;
      obtain, using the non-invasive measurement sub-system, heart rate-derived data for the user over a period of time;
      correlate, through the predictive model, patterns in the heart rate-derived data with events in the menstrual cycle;
      provide the heart rate-derived data as additional input to the predictive model;
      generate, using the predictive model and the additional input, an updated prediction for the future event related to the menstrual cycle, the predictive model using machine learning to analyze the heart-rate derived data, and the historical user information being used to refine or retrain the predictive model; and
      display, on the display device, information associated with the updated prediction for the future event.

2. The system of claim 1, wherein the instructions when executed further cause the system to:
   receive indication of an occurrence of an event associated with the menstrual cycle of the user; and update the predictive model for the menstrual cycle based at least in part upon the indication.

3. The system of claim 1, wherein the instructions when executed further cause the system to:
monitor the heart rate-derived data over a future period of time;
determine, during the future period of time, that at least one value of the heart rate-derived data is associated with a correlated event for a menstrual cycle; and
provide an updated prediction for the correlated event based at least in part upon the at least one value.

4. The system of claim 1, wherein the instructions when executed further cause the system to:
obtain additional health data for the user for use in generating and updating the predictive model, the additional health data including at least one of hemoglobin concentration, blood oxygen concentration level, body temperature, heart rate variability (HRV) metrics, respiration rate, electrodermal activity, hormone level, sleep quality, activity level, step count, weight, time of the year, location, body mass index, or age information.

5. The system of claim 1, wherein the instructions when executed further cause the system to:
obtain the heart rate-derived data using near-infrared (NIR) or short-wave infrared (SWIR) spectroscopy with light of at least one wavelength between about 900 nm and about 1500 nm.

6. A computer-implemented method, comprising:
obtaining historical information related to a menstrual cycle of a user;
determining, based at least in part on the historical information, a predictive model for the menstrual cycle;
obtaining, using a non-invasive measurement system of a monitoring device, heart rate data for the user;
automatically determining, based at least in part on the heart rate data and the predictive model, at least one pattern in the heart rate data;
determining, based at least in part on the at least one pattern and the predictive model, an updated predictive model;
determining, based at least in part on the updated predictive model, a future event related to the menstrual cycle, the updated predictive model using machine learning to analyze the heart-rate derived data, and the historical user information being used to refine or retrain the updated predictive model; and
presenting, on the monitoring device, the future event.

7. The computer-implemented method of claim 6, further comprising:
receiving, from the user, a selection of one or more types of events for which to receive the historical information, the types of events including occurrences of menstruation or ovulation.

8. The computer-implemented method of claim 6, further comprising:
receiving an indication of an occurrence of an event associated with the menstrual cycle of the user; and
updating the predictive model based at least in part upon the indication.

9. The computer-implemented method of claim 6, further comprising:
monitoring the heart rate data over a future period of time;
determining, during the future period of time, that at least one value of the heart rate data is associated with a correlated menstrual cycle event; and
updating the predictive model based at least in part on the correlated tenst event.

10. The computer-implemented method of claim 6, further comprising:
obtaining additional health data for the user for use in generating and updating the predictive model, the additional health data including at least one of hemoglobin concentration, blood oxygen concentration level, body temperature, heart rate variability (HIRV) metrics, respiration rate, electrodermal activity, hormone level, sleep quality, activity level, step count, weight, height, time of the year, location, body mass index, or age information.

11. The computer-implemented method of claim 6, further comprising:
obtaining the heart rate data using an optical sub-system including at least one optical emitter and at least one optical detector, the optical detector configured to detect light from the optical emitter that is not absorbed by the skin of the user.

12. The computer-implemented method of claim 6, further comprising:
generating the predictive model based at least in part on the historical information related to a menstrual cycle of a user.

13. The computer-implemented method of claim 6, wherein the monitoring device includes at least one of a smart watch, a fitness band, a tracker ring, an earbud, smart clothing, a scale, a body composition analyzer, an electrodermal sensor, or smart bedding.

14. The computer-implemented method of claim 6, further comprising:
obtaining, using at least one motion sensor of the monitoring device, motion data for the user; and
excluding from consideration the heart rate data for a determined period of time corresponding to motion of the user.

15. The computer-implemented method of claim 6, further comprising:
obtaining the heart rate data using near-infrared (NIR) spectroscopy with light of at least one wavelength between about 900 nm and about 1500 nm.

16. A non-transitory computer-readable storage medium including instructions that, when executed by at least one processor, cause the at least one processor to:
obtain historical user information for one or more events related to a menstrual cycle of a user;
generate a prediction for a future event related to the menstrual cycle, the prediction based at least in part on the historical user information as input into a predictive model;
obtain, using a non-invasive measurement sub-system of a monitoring device, heart rate-derived data for the user over a period of time;
correlate, through the predictive model, patterns in the heart rate-derived data with events in the menstrual cycle;
provide the heart rate-derived data as additional input to the predictive model; and
generate, using the predictive model and the additional input, an updated prediction for the future event related to the menstrual cycle the predictive model using machine learning to analyze the heart-rate derived data, and the historical user information being used to refine or retrain the predictive model.

17. The non-transitory computer-readable storage medium of claim 16, wherein the instructions, when executed, further cause the at least one processor to:

update the predictive model using at least one of the additional input or information about an actual timing of the future event.

18. The non-transitory computer-readable storage medium of claim 16, wherein the instructions, when executed; further cause the at least one processor to:
   obtain the heart rate-derived data using an optical photoplethsymogram (PPG) of the monitoring device as worn by the user, the PPG operable to determine changes in absorption of the light in skin of the user.

19. The non-transitory computer-readable storage medium of claim 16, wherein the instructions, when executed, further cause the at least one processor to:
   obtain motion data for the user using at least one motion sensor of the monitoring device.

20. The non-transitory computer-readable storage medium of claim 16, wherein the instructions, when execute$_d$; further cause the at least one processor to:
   obtain additional health data for the user; and
   use the additional health data to train and update the predictive model, the additional health data including at least one of hemoglobin concentration, blood oxygen concentration level, heart rate variability (HRV) metrics, respiration rate, electrodermal activity, body temperature, hormone level, sleep quality, activity level, step count, weight, height, time of the year, location body mass index, or age information.

\* \* \* \* \*